US008380300B2

(12) United States Patent
Gerber et al.

(10) Patent No.: US 8,380,300 B2
(45) Date of Patent: Feb. 19, 2013

(54) EFFICACY VISUALIZATION

(75) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1298 days.

(21) Appl. No.: 11/414,538

(22) Filed: Apr. 28, 2006

(65) Prior Publication Data
US 2007/0255321 A1    Nov. 1, 2007

(51) Int. Cl.
*A61N 1/00*    (2006.01)
(52) U.S. Cl. ............................................. 607/2
(58) Field of Classification Search .................. 607/50, 607/30, 59; 600/513
See application file for complete search history.

(56) References Cited

U.S. PATENT DOCUMENTS

| | | |
|---|---|---|
| 4,236,524 A | 12/1980 | Powell et al. |
| 4,872,122 A | 10/1989 | Altschuler et al. |
| 4,895,574 A | 1/1990 | Rosenberg |
| 5,005,143 A | 4/1991 | Altschuler et al. |
| 5,240,009 A | 8/1993 | Williams |
| 5,280,792 A | 1/1994 | Leong et al. |
| 5,358,513 A | 10/1994 | Powell, III et al. |
| 5,383,910 A | 1/1995 | den Dulk |
| 5,443,486 A | 8/1995 | Hrdlicka et al. |
| 5,522,863 A | 6/1996 | Spano et al. |
| 5,626,140 A | 5/1997 | Feldman et al. |
| 5,645,069 A | 7/1997 | Lee |
| 5,673,367 A | 9/1997 | Buckley |
| 5,702,429 A | 12/1997 | King |
| 5,706,403 A | 1/1998 | Shibata et al. |
| 5,713,932 A | 2/1998 | Gillberg et al. |
| 5,716,382 A | 2/1998 | Snell |
| 5,774,357 A | 6/1998 | Hoffberg et al. |
| 5,782,885 A | 7/1998 | Andersson |
| 5,810,014 A | 9/1998 | Davis et al. |

(Continued)

FOREIGN PATENT DOCUMENTS

| | | |
|---|---|---|
| EP | 0 590 200 | 4/1994 |
| EP | 0 653 224 A2 | 5/1995 |

(Continued)

OTHER PUBLICATIONS

Office Action dated Jul 10, 2008 for U.S. Appl. No. 11/414,616 (13 pgs.).

(Continued)

*Primary Examiner* — Eric D. Bertram
*Assistant Examiner* — Elizabeth K So
(74) *Attorney, Agent, or Firm* — Schumaker & Sieffert, PA

(57) ABSTRACT

The disclosure is directed to techniques for providing a visualization of efficacy ratings for a medical therapy. A graphical representation of weighted efficacy parameter values may be displayed to provide a visualization of efficacy for the patient. The graphical representation may include a boundary extending between the efficacy parameter values on multiple axes. If the representation includes three axes, the shape of the boundary may be substantially triangular. The graphical representation may simultaneously display multiple graphical representations. Each of the multiple multi-axis graphical representations corresponds to efficacy parameter values obtained for different sets of therapy parameters or to efficacy parameter values obtained at different times. The graphical representation may be modified so that the efficacy parameter values correspond to values relating to a time reference specified by a user. Multiple graphical representations for different time references may be displayed simultaneously, permitting the user to compare efficacy over time.

32 Claims, 17 Drawing Sheets

U.S. PATENT DOCUMENTS

| | | | |
|---|---|---|---|
| 5,867,386 A | 2/1999 | Hoffberg et al. |
| 5,875,108 A | 2/1999 | Hoffberg et al. |
| 5,901,246 A | 5/1999 | Hoffberg et al. |
| 5,903,454 A | 5/1999 | Hoffberg et al. |
| 5,920,477 A | 7/1999 | Hoffberg et al. |
| 5,921,937 A | 7/1999 | Davis et al. |
| 5,938,688 A | 8/1999 | Schiff |
| 5,938,690 A | 8/1999 | Law et al. |
| 5,995,868 A | 11/1999 | Dorfmeister et al. |
| 5,999,854 A | 12/1999 | Deno et al. |
| 6,021,352 A | 2/2000 | Christopherson et al. |
| 6,038,476 A | 3/2000 | Schwartz |
| 6,066,163 A | 5/2000 | John |
| 6,081,750 A | 6/2000 | Hoffberg et al. |
| 6,129,745 A | 10/2000 | Sun et al. |
| 6,171,239 B1 | 1/2001 | Humphrey |
| 6,192,273 B1 | 2/2001 | Igel et al. |
| 6,205,360 B1 | 3/2001 | Carter et al. |
| 6,263,230 B1 | 7/2001 | Haynor et al. |
| 6,269,267 B1 | 7/2001 | Bardy et al. |
| 6,308,102 B1 | 10/2001 | Sieracki et al. |
| 6,345,200 B1 | 2/2002 | Mouchawar et al. |
| 6,370,423 B1 | 4/2002 | Guerrero et al. |
| 6,385,479 B1 | 5/2002 | Sibbitt et al. |
| 6,386,882 B1 | 5/2002 | Linberg |
| 6,400,996 B1 | 6/2002 | Hoffberg et al. |
| 6,408,290 B1 | 6/2002 | Thiesson et al. |
| 6,418,424 B1 | 7/2002 | Hoffberg et al. |
| 6,434,261 B1 | 8/2002 | Zhang et al. |
| 6,438,418 B1 | 8/2002 | Swerdlow et al. |
| 6,456,622 B1 | 9/2002 | Skaanning et al. |
| 6,473,653 B1 | 10/2002 | Schallhorn et al. |
| 6,480,743 B1 | 11/2002 | Kirkpatrick et al. |
| 6,480,814 B1 | 11/2002 | Levitan |
| 6,496,816 B1 | 12/2002 | Thiesson et al. |
| 6,497,655 B1 | 12/2002 | Linberg et al. |
| 6,522,928 B2 | 2/2003 | Whitehurst et al. |
| 6,530,954 B1 | 3/2003 | Eckmiller |
| 6,539,249 B1 | 3/2003 | Kadhiresan et al. |
| 6,539,263 B1 | 3/2003 | Schiff et al. |
| 6,547,746 B1 | 4/2003 | Marino |
| 6,549,804 B1 | 4/2003 | Osorio et al. |
| 6,554,762 B2 | 4/2003 | Leysieffer |
| 6,556,699 B2 | 4/2003 | Rogers et al. |
| 6,572,542 B1 | 6/2003 | Houben et al. |
| 6,575,894 B2 | 6/2003 | Leysieffer et al. |
| 6,597,943 B2 | 7/2003 | Taha et al. |
| 6,609,017 B1 | 8/2003 | Shenoy et al. |
| 6,612,983 B1 | 9/2003 | Marchal |
| 6,658,287 B1 | 12/2003 | Litt et al. |
| 6,659,968 B1 | 12/2003 | McClure |
| 6,662,051 B1 | 12/2003 | Eraker et al. |
| 6,687,538 B1 | 2/2004 | Hrdlicka et al. |
| 6,697,672 B2 | 2/2004 | Andersson |
| 6,704,595 B2 | 3/2004 | Bardy |
| 7,050,856 B2 | 5/2006 | Stypulkowski |
| 7,123,961 B1 | 10/2006 | Kroll et al. |
| 7,142,923 B2 | 11/2006 | North et al. |
| 7,142,923 B2 | 11/2006 | Benser et al. |
| 7,167,743 B2 | 1/2007 | Heruth et al. |
| 2002/0016699 A1 | 2/2002 | Hoggart et al. |
| 2002/0038294 A1 | 3/2002 | Matsugu |
| 2002/0045804 A1 | 4/2002 | Christopherson et al. |
| 2002/0055779 A1 | 5/2002 | Andrews |
| 2002/0087201 A1 | 7/2002 | Firlik et al. |
| 2002/0091419 A1 | 7/2002 | Firlik et al. |
| 2002/0103512 A1 | 8/2002 | Echauz et al. |
| 2002/0123673 A1 | 9/2002 | Webb et al. |
| 2002/0138013 A1 | 9/2002 | Guerrero et al. |
| 2002/0140728 A1 | 10/2002 | Zimmerman |
| 2002/0151992 A1 | 10/2002 | Hoffberg et al. |
| 2002/0177882 A1 | 11/2002 | DiLorenzo |
| 2003/0041866 A1 | 3/2003 | Linberg et al. |
| 2003/0043815 A1 | 3/2003 | Tinsley et al. |
| 2003/0050568 A1 | 3/2003 | Green et al. |
| 2003/0053663 A1 | 3/2003 | Chen et al. |
| 2003/0078632 A1 | 4/2003 | Ujhelyi et al. |
| 2003/0083716 A1 | 5/2003 | Nicolelis et al. |
| 2003/0088274 A1 | 5/2003 | Gliner et al. |
| 2003/0093129 A1 | 5/2003 | Nicolelis et al. |
| 2003/0097159 A1 | 5/2003 | Schiff et al. |
| 2003/0097161 A1 | 5/2003 | Firlik et al. |
| 2003/0105409 A1 | 6/2003 | Donoghue et al. |
| 2003/0135248 A1 | 7/2003 | Stypulkowski |
| 2003/0144711 A1 | 7/2003 | Pless et al. |
| 2003/0158587 A1 | 8/2003 | Esteller et al. |
| 2003/0163353 A1 | 8/2003 | Luce et al. |
| 2003/0195569 A1 | 10/2003 | Swerdlow et al. |
| 2003/0216620 A1 | 11/2003 | Jain et al. |
| 2003/0216654 A1 | 11/2003 | Xu et al. |
| 2004/0103001 A1 | 5/2004 | Mazar et al. |
| 2004/0111131 A1 | 6/2004 | Hu et al. |
| 2004/0129271 A1 | 7/2004 | Hickle |
| 2004/0143302 A1 | 7/2004 | Sieracki et al. |
| 2004/0164983 A1 | 8/2004 | Khozai |
| 2004/0199217 A1 | 10/2004 | Lee et al. |
| 2004/0215288 A1 | 10/2004 | Lee et al. |
| 2004/0267330 A1 | 12/2004 | Lee et al. |
| 2004/0267818 A1 | 12/2004 | Hartenstine |
| 2005/0043774 A1 | 2/2005 | Devlin et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0075669 A1 | 4/2005 | King |
| 2005/0080462 A1 | 4/2005 | Jenkins et al. |
| 2005/0177206 A1 | 8/2005 | North et al. |
| 2005/0222643 A1 | 10/2005 | Heruth et al. |
| 2005/0245987 A1 | 11/2005 | Woods et al. |
| 2005/0245988 A1 | 11/2005 | Miesel |
| 2005/0288728 A1 | 12/2005 | Libbus et al. |
| 2006/0020292 A1 | 1/2006 | Goetz et al. |
| 2006/0190047 A1 | 8/2006 | Gerber et al. |
| 2006/0190048 A1 | 8/2006 | Gerber |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0190061 A1 | 8/2006 | Stypulkowski |
| 2006/0195145 A1 | 8/2006 | Lee et al. |
| 2006/0195152 A1 | 8/2006 | Gerber |
| 2006/0206162 A1 | 9/2006 | Wahlstrand et al. |
| 2006/0206163 A1 | 9/2006 | Wahlstrand et al. |
| 2006/0235472 A1 | 10/2006 | Goetz et al. |
| 2006/0259099 A1 | 11/2006 | Goetz et al. |
| 2006/0270944 A1 | 11/2006 | King |
| 2007/0112404 A1 | 5/2007 | Mann et al. |
| 2007/0245318 A1 | 10/2007 | Goetz et al. |
| 2007/0255322 A1 | 11/2007 | Gerber et al. |

FOREIGN PATENT DOCUMENTS

| | | |
|---|---|---|
| EP | 0 541 338 B1 | 9/1996 |
| EP | 0 756 877 A2 | 2/1997 |
| EP | 0 796 636 A1 | 9/1997 |
| EP | 0 684 858 B1 | 4/1998 |
| EP | 0 848 965 A2 | 6/1998 |
| EP | 0 882 469 B1 | 9/2002 |
| EP | 0 848 965 B1 | 8/2003 |
| EP | 0 653 224 B1 | 1/2004 |
| EP | 1 192 971 B1 | 1/2005 |
| WO | WO 84/02458 | 7/1984 |
| WO | WO 9841270 | 9/1998 |
| WO | WO 98/49647 | 11/1998 |
| WO | WO 98/49647 A1 * | 11/1998 |
| WO | WO 00/10455 A1 | 3/2000 |
| WO | WO 01/17419 A1 | 3/2001 |
| WO | WO 01/43823 A1 | 6/2001 |
| WO | WO 01/47600 A1 | 7/2001 |
| WO | WO 01/56467 A1 | 8/2001 |
| WO | WO 01/60445 A2 | 8/2001 |
| WO | WO 01/82995 A2 | 11/2001 |
| WO | WO 01/82995 A3 | 11/2001 |
| WO | WO 02/02622 A2 | 1/2002 |
| WO | WO 02/15777 A1 | 2/2002 |
| WO | WO 03/043690 A1 | 5/2003 |
| WO | WO 03/051175 A2 | 6/2003 |
| WO | WO 03/094721 A1 | 11/2003 |
| WO | WO 2004/039449 | 5/2004 |

| WO | WO 2004/041352 A1 | 5/2004 |
| --- | --- | --- |
| WO | WO 2004/075982 A1 | 9/2004 |
| WO | WO 2004/096349 A1 | 11/2004 |
| WO | WO 2004/096358 A2 | 11/2004 |
| WO | WO 2005/028028 A1 | 3/2005 |
| WO | WO 2005/039388 | 5/2005 |
| WO | WO 2005/039688 A2 | 5/2005 |
| WO | WO 2005/089646 | 9/2005 |
| WO | WO 2005/089647 | 9/2005 |
| WO | WO 2006/012423 | 2/2006 |
| WO | WO 2006/012423 A1 | 2/2006 |
| WO | WO 2006/098823 A1 | 9/2006 |
| WO | WO 2006/098824 A1 | 9/2006 |

OTHER PUBLICATIONS

Responsive Amendmen dated Oct. 10, 2008 for U.S. Appl. No. 11/414,616 (6 pgs.).
Office Action dated Jan. 22, 2009 for U.S. Appl. No. 11/414,616 (6 pgs.).
Responsive Amendment dated Apr. 22, 2009 for U.S. Appl. No. 11/414,616 (15 pgs.).
Notification of Transmittal of the International Preliminary Report on Patentability dated Jun. 23, 2008 for Application No. PCT/US2007/001936 (12 pgs.).
Notification of Transmittal of the International Search Report and the Written Opinion of the International Searching Authority for corresponding patent application No. PCT/US2007/001936, mailed Jul. 2, 2007, (13 pages).
Office Action dated Jul. 29, 2009 for U.S. Appl. No. 11/414,616 (8 pgs.).
Responsive Amendment dated Oct. 23, 2009 for U.S. Appl. No. 11/414,616 (17 pgs.).
Office Action dated Jan. 15, 2010 for U.S. Appl. No. 11/414,616 (8 pgs.).
Responsive Amendment dated Apr. 15, 2010 for U.S. Appl. No. 11/414,616 (17 pgs.).
Office Action dated Jul. 19, 2010 for U.S. Appl. No. 11/414,616 (8 pgs.).
Responsive Amendment dated Sep. 17, 2010 for U.S. Appl. No. 11/414,616 (18 pgs.).
European Examination Report from EP Application No. 07 749 183.5, mailed Oct. 18, 2010, 12 pgs.
Responsive Amendment from corresponding EP Application No. 07 749 179.3, dated Jan. 19, 2011, 9 pages.
Laibovitz et al., "Comparison of Quality of Life and Patient Preference of Dorzolamide and Pilocarpine as Adjunctive Therapy to Timolol in the Treatment of Glaucoma," Journal of Glaucoma, 4:306-313, Lippincott-Raven Publishers, Philadelphia, 1995, 8 pages.
European Office Action dated Jul. 29, 2010 for corresponding Application No. 07 749 179.3, (6 pgs.).
Communication dated Mar. 28, 2012 for corresponding European Application No. 07749183.5, (8 pgs.).
Response to Examination Report dated Apr. 20, 2011 for European Application No. 07749183.5, (8 pgs.).
Notification of Transmittal of the International Search Report and the Written Opinion of the International Searching Authority dated Jul. 3, 2007 for PCT Application No. PCT/US2007/001940, (13 pgs.).
Notification of Transmittal of the International Preliminary Report on Patentability dated Jul. 10, 2008 for PCT Application No. PCT/US2007/001940, (15 pgs.).

\* cited by examiner

EFFICACY VISUALIZATION

TECHNICAL FIELD

The invention relates to implantable medical devices and, more particularly, electrical stimulation therapy.

BACKGROUND

Implantable electrical stimulators may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, an implantable stimulator delivers electrical stimulation therapy in the form of electrical pulses. An implantable stimulator may deliver electrical stimulation therapy via one or more leads carrying electrodes located proximate to target locations associated with the brain, the spinal cord, pelvic nerves, peripheral nerves, or the stomach of a patient. Hence, stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES) to promote muscle movement or prevent atrophy.

A clinician selects values for a number of programmable parameters in order to define the electrical stimulation therapy to be delivered by the implantable stimulator to a patient. For example, the clinician ordinarily selects a combination of electrodes carried by one or more implantable leads, and assigns polarities to the selected electrodes. In addition, the clinician selects an amplitude, which may be a current or voltage amplitude, a pulse width and a pulse rate for stimulation pulses to be delivered to the patient. A group of parameters, including electrode combination, electrode polarity, amplitude, pulse width and pulse rate, may be referred to as a program in the sense that they control the electrical stimulation therapy delivered to the patient. In some applications, an implantable stimulator may deliver stimulation therapy according to multiple programs either simultaneously or on a time-interleaved, overlapping or non-overlapping, basis.

The process of selecting a program can be time consuming. The clinician typically will evaluate a variety of electrode combinations, polarities and parameter values to identify an acceptable program. The clinician selects a program that balances effectiveness of the therapy in relieving symptoms with the presence of undesirable side effects. In addition, to some extent, efficacy may be rated in terms of the amount of power consumed by a program. For example, among programs providing equivalent effectiveness and side effects, programs that tend to conserve power may be considered superior. To achieve an acceptable level of efficacy, a clinician must evaluate various stimulation parameters and accurately track results.

SUMMARY

The disclosure is directed to techniques for providing a patient-individualized efficacy rating and efficacy visualization. Different stimulation parameters impact efficacy. For example, for electrical stimulation therapy, efficacy may be a function of stimulation parameters such as electrode combination, electrode polarity, current or voltage amplitude, pulse width, and pulse rate. In addition, efficacy may vary from patient-to-patient. For example, efficacy of stimulation therapy may vary according to patient age, gender, physiology, disease state, activity level, or activity profile.

Comparable stimulation program may provide different levels of efficacy for different patients, in accordance with individualized patient characteristics or desires. Patients may rank efficacy parameters differently. The efficacy parameters may include both desirable therapeutic effects and undesirable side effects. For one patient, optimization of a particular efficacy parameter may be the paramount concern. Other patients may be willing to compromise the outcome of the same parameter in favor of better outcomes with other efficacy parameters.

As one illustration, efficacy of urinary incontinence therapy may be defined by the following set of efficacy parameters: urination frequency, nocturia and incontinent episodes. One patient may find nocturia most undesirable, and prioritize minimization of nocturia above other parameters. For example, the patient may rank the importance of the parameters as (1) nocturia, (2) incontinent episodes, and (3) frequency. Another patient, however, may view avoidance of incontinence episodes as the most important factor, followed by nocturia and frequency. The latter patient may tolerate nocturia and frequency provided the program minimizes incontinent episodes.

Another patient may likewise rank minimization of incontinent episodes as the most important factor, but specify an acceptable severity index. For example, the patient may desire elimination of large volume incontinent episodes but tolerate small leakage. If large volume incontinent episodes are eliminated, the patient may seek to next address nocturia. To accommodate patient differences, it is desirable to provide a patient-individualized efficacy rating that rates efficacy not solely according to an absolute objective scale, but according to the individual needs and desires of the patient, subject to the clinician's judgment.

To provide a patient-individualized efficacy rating, in accordance with this disclosure, a patient may assign weighting values to a list of efficacy parameters. For a given therapy, the list of efficacy parameters may be fixed from patient-to-patient or specified for each patient. The weighting values are applied to efficacy parameter values to produce a patient-individualized efficacy rating. A clinician also may assign weighting values to the efficacy parameters, either alone or in combination with weighting values specified by the patient.

A multi-axis graphical representation of the weighted efficacy parameter values may be displayed to provide a visualization of the efficacy for the patient. The multi-axis graphical representation may include a boundary extending between the efficacy parameter values on the multiple axes, wherein the boundary defines a shape. If the multi-axis representation includes three axes, the shape of the boundary may be substantially triangular.

In some cases, the graphical representation may simultaneously display multiple multi-axis graphical representations of the efficacy parameter values, wherein each of the multiple multi-axis graphical representations corresponds to efficacy parameter values obtained for different sets of stimulation parameters or to efficacy parameter values obtained at different times.

In other embodiments, the graphical representation may modify a graphical representation of efficacy parameter values to correspond to values relating to a time reference specified by a user. Multiple graphical representations for different time references may be displayed simultaneously, permitting the user to compare efficacy over time.

In one embodiment, the disclosure provides a method comprising obtaining values of a plurality of efficacy parameters associated with therapy delivered to a patient, and displaying a multi-axis graphical representation of the efficacy parameter values, wherein each of the efficacy parameters is represented along one of the axes.

In another embodiment, the disclosure provides a device comprising a processor that obtains values of a plurality of efficacy parameters associated with therapy delivered to a patient, and a user interface that displays a multi-axis graphical representation of the efficacy parameter values, wherein each of the efficacy parameters is represented along one of the axes.

In an additional embodiment, the disclosure provides a computer-readable medium comprising instructions to cause a processor to obtain values of a plurality of efficacy parameters associated with therapy delivered to a patient, and control a user interface to display a multi-axis graphical representation of the efficacy parameter values, wherein each of the efficacy parameters is represented along one of the axes.

In a further embodiment, the disclosure provides a method comprising obtaining values of a plurality of efficacy parameters associated with therapy delivered to a patient, displaying a graphical representation of the efficacy parameter values, wherein each of the efficacy parameters is represented along one of the axes, receiving input indicating a time reference for the efficacy parameter values, and modifying the graphical representation of the efficacy parameter values to correspond to efficacy parameter values relating to the time reference.

In another embodiment, the disclosure provides a processor that obtains values of a plurality of efficacy parameters associated with therapy delivered to a patient, and a user interface that displays a graphical representation of the efficacy parameter values, wherein each of the efficacy parameters is represented along one of the axes, wherein the processor receives input indicating a time reference for the efficacy parameter values, and modifies the graphical representation of the efficacy parameter values to correspond to efficacy parameter values relating to the time reference.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
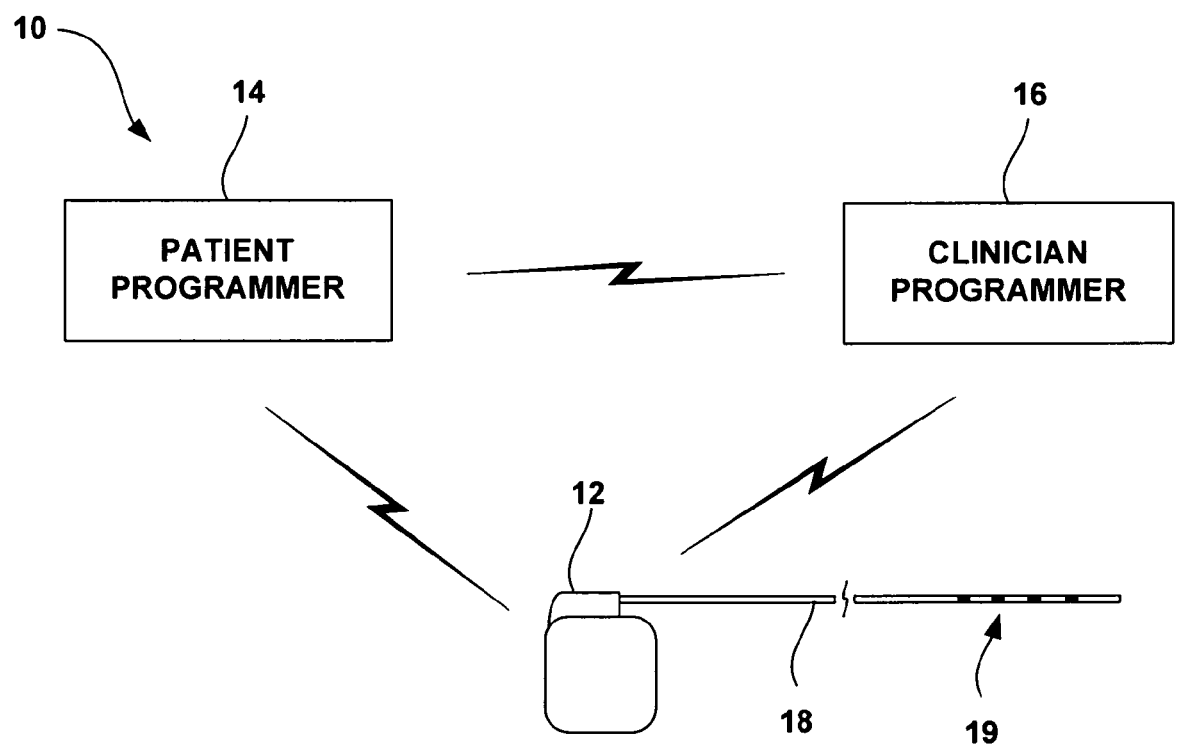
FIG. 1 is a schematic diagram illustrating an implantable electrical stimulation system including an implantable stimulator, a patient programmer and a clinician programmer.

Medical therapies, such as electrical stimulation therapy, may provide relief to a patient from many conditions. However, the stimulation therapy efficacy is contingent on a clinician correctly configuring, or programming, the stimulation parameters in a manner that provides therapy to the patient while minimizing side-effects produced from the stimulation. Efficacy may be judged in terms of the extent to which therapy relieves symptoms or a disorder or disease, in combination with the absence of undesirable side effects. Due to differences in patient age, gender, physiology, disease state, activity level, or activity profile, the parameters supporting effective therapy may vary greatly between patients.

Moreover, the perception of efficacy may vary from patient to patient. In particular, comparable stimulation programs may provide different levels of efficacy for different patients, in accordance with individualized patient characteristics or desires. In addition, different patients may rank efficacy parameters differently. For one patient, optimization of a particular efficacy parameter may be the paramount concern. Other patients may be willing to compromise the outcome of the same parameter in favor of better outcomes with other efficacy parameters. The disclosure provides techniques for patient-individualized efficacy rating so that efficacy and associated stimulation parameters can be customized to individual patients.

To provide a patient-individualized efficacy rating, the techniques described in this disclosure permit assignment of weighting values to a list of efficacy parameters. For a given therapy, the list of efficacy parameters may be fixed from patient-to-patient or specified for each patient. The weighting values are applied to efficacy parameter values to produce a patient-individualized efficacy rating. A clinician also may assign weighting values to the efficacy parameters, either alone or in combination with weighting values specified by the patient. A multi-axis graphical representation of the weighted efficacy parameter values may be displayed to provide a visualization of the efficacy for the patient.

The techniques described herein may be used during a test or evaluation mode of an electrical stimulator to select different stimulation parameters in an effort to identify a program providing acceptable efficacy. For example, the techniques and associated user interfaces may be implemented in a clinician programmer used by a clinician to program a stimulator, in a patient programmer used by a patient to program or control a stimulator, or in an external stimulator including both pulse generation and programming functionality. As a further alternative, the efficacy rating and visualization techniques described herein are not necessarily limited to use with implantable stimulators, and may be used in conjunction with external stimulators that deliver stimulation, e.g., via percutaneous leads.

The efficacy rating and visualization techniques described in this disclosure may be applicable to any of a variety of electrical stimulation therapies. For ease of illustration, and purposes of example, however, the efficacy rating and visualization techniques will be described in terms of application to electrical stimulation therapies for urinary incontinence. Urinary incontinence, or an inability to control urinary function, is a common problem afflicting people of all ages, genders, and races. Various muscles, nerves, organs and conduits within the urinary tract cooperate to collect, store and release urine. A variety of disorders may compromise urinary tract performance and contribute to incontinence. Many of the disorders may be associated with aging, injury or illness.

Electrical stimulation of nerves in the pelvic floor may provide an effective therapy for a variety of disorders, including urinary incontinence. For example, an implantable electrical stimulator may be to deliver electrical stimulation to the sacral nerve to induce sphincter constriction and thereby close or maintain closure of the urethra at the bladder neck. In addition, electrical stimulation of the bladder wall may enhance pelvic floor muscle tone and assist fluid retention in the bladder or voiding fluid from the bladder.

Parameters useful in evaluating efficacy of electrical stimulation for urinary incontinence therapy include incontinent episodes, urination frequency, and nocturia. Incontinent episodes may be evaluated, for example, in terms of the number of episodes in a given time frame. Urination frequency may be evaluated, likewise, in terms of the number of voiding events by a patient within a given time frame. Nocturia may refer to the number of nighttime voluntary and/or involuntary voiding events experienced by the patient with the pertinent time frame. Undesirable side effects that may be considered efficacy parameters include pain, an undesirable sensory feeling such as parasthesia, and sexual dysfunction. Other parameters may include battery depletion rate, retention, and/or constipation.

The disclosure describes systems and methods to help quantify and visualize incontinence efficacy measures. The efficacy of therapy for incontinence should be quantifiable in a straightforward way before it can be visualized in a simple and meaningful way. However, the multimodal nature of incontinence disorders, side effects introduced by treatments, and the fact that incontinence is primarily a quality of life issue that may not be directly quantified by measuring parameters such as leaks can make rating and analysis complex endeavors.

Once efficacy priorities and side effect invasiveness are identified, the framework for describing the overall efficacy can be presented. As one example, an overall efficacy description may effectively sum the weighted efficacy goodness achieved less the weighted side-effect badness caused using weights established by a user such as a patient and/or clinician In this disclosure, a user may include a patient or a clinician. Also, the term clinician may include physician, other medical care-givers such as physician's assistants, nurses, and medical technicians.

The patient and clinician profiles may be aggregated and displayed or displayed separately. An efficacy rating score may be expressed as follows:

$$\text{Score} = \sum_{0}^{N} (w_n \cdot \text{EfficacyGoodness}) - \sum_{0}^{N} (w_n \cdot \text{SideEffectBadness})$$

where Efficacy Goodness represents the efficacy parameter value for a given beneficial efficacy parameter, such as a parameter presenting an improvement in incontinent episodes, SideEffectBadness represents the efficacy parameter value for a given side effect efficacy parameter, such as pain or sexual dysfunction.

So that the overall efficacy rating score has more inherent meaning, it can be scaled on a per-parameter and overall basis to describe key milestones or goals of treatment. For example, each parameter score can be scaled such that a 50% improvement corresponds to a particular value such as 100. Similarly, the overall efficacy rating score may be scaled to such external standards or may be customized to meet the needs of each patient and clinician. The badness of side effects can be similarly decomposed into scaled performance factors on a per-parameter basis and integrated into the overall score according to the relative badness of each.

As an alternative to rating SideEffectBadness as a negative, it may be inverted such that an improvement in a side effect parameter is presented as a positive value and summed with the EfficacyGoodness value. In this case, all efficacy parameter values may be handled as positive values representing improvement relative to a baseline, and there is no need to distinguish between good parameter values and bad parameter values. Still, the above equation may be useful in analyzing the overall efficacy rating problem. In general, the goodness of a particular efficacy parameter (e.g., number of leaks) could be determined either by an absolute improvement (3 less leaks per unit time relative to an established pre-therapy baseline) or by the relative improvement (X % fewer leaks relative to baseline).

In addition to measurable conditions such as incontinent episodes, urination frequency and nocturia, for example, the system and methods described in this disclosure alternatively or additionally may be adapted to integrate objective patient feedback such as input in the form of quality of life (QOL) survey data. Such information can easily be gathered QOL feedback mechanisms such as the SF-36 survey. The SF-36 is a multi-purpose, short-form health survey with only 36 questions, providing an 8-scale profile of functional health and well-being scores, and psychometrically-based physical and mental health summary measures and a preference-based health utility index.

FIG. 1 is a schematic diagram illustrating an implantable electrical stimulation system 10 including an implantable stimulator 12, a patient programmer 14 and a clinician programmer 16. Implantable stimulator 12 includes one or more leads 18 carrying one or more electrodes. As In the example of FIG. 1, lead 18 includes a plurality of ring electrodes 19 adjacent a distal end of the lead. The lead 18 is implanted and tunneled through patient tissue to place ring electrodes 19 in close proximity to a target stimulation site, such as sacral nerve site. Sacral nerve stimulation may result in an increase in pelvic floor muscle tone or the contraction of the urinary sphincter, which keeps urine inside the bladder to avoid incontinence.

Patient programmer 14 may be constructed as a portable device that accompanies the patient throughout a daily routine. Patient programmer 14 communicates with stimulator 12 by wireless telemetry. The patient may operate patient programmer 14 to adjust stimulation parameters, such as amplitude, pulse width and pulse rate, or select different programs for application by stimulator 12. In some embodiments, the patient may enter information into the patient programmer 14, e.g., for evaluation by a clinician either remotely or during a clinic visit. For example, the patient may enter efficacy ratings as the patient experiences the effects of the therapy applied by stimulator 12. Also, for the example of urinary incontinence therapy, the patient may enter voiding diary information indicating times at which the patient voluntarily or involuntarily voids urine.

Clinician programmer 16 is used by a clinician to program stimulator 12 and control the stimulator to apply different programs and parameters to evaluate efficacy. Clinician programmer 16 communicates with stimulator 12 by wireless telemetry. In addition, clinician programmer 16 may be configured to accept input from the clinician and/or patient relating to efficacy ratings, weighting values, and the like. In some embodiments, clinician programmer 16 also may display graphical imagery that provides efficacy visualization for the clinician and/or patient. Clinician programmer 16 also may communicate with patient programmer 14 by wired or wireless media, e.g., to download application or operating system updates.

Figure 2:
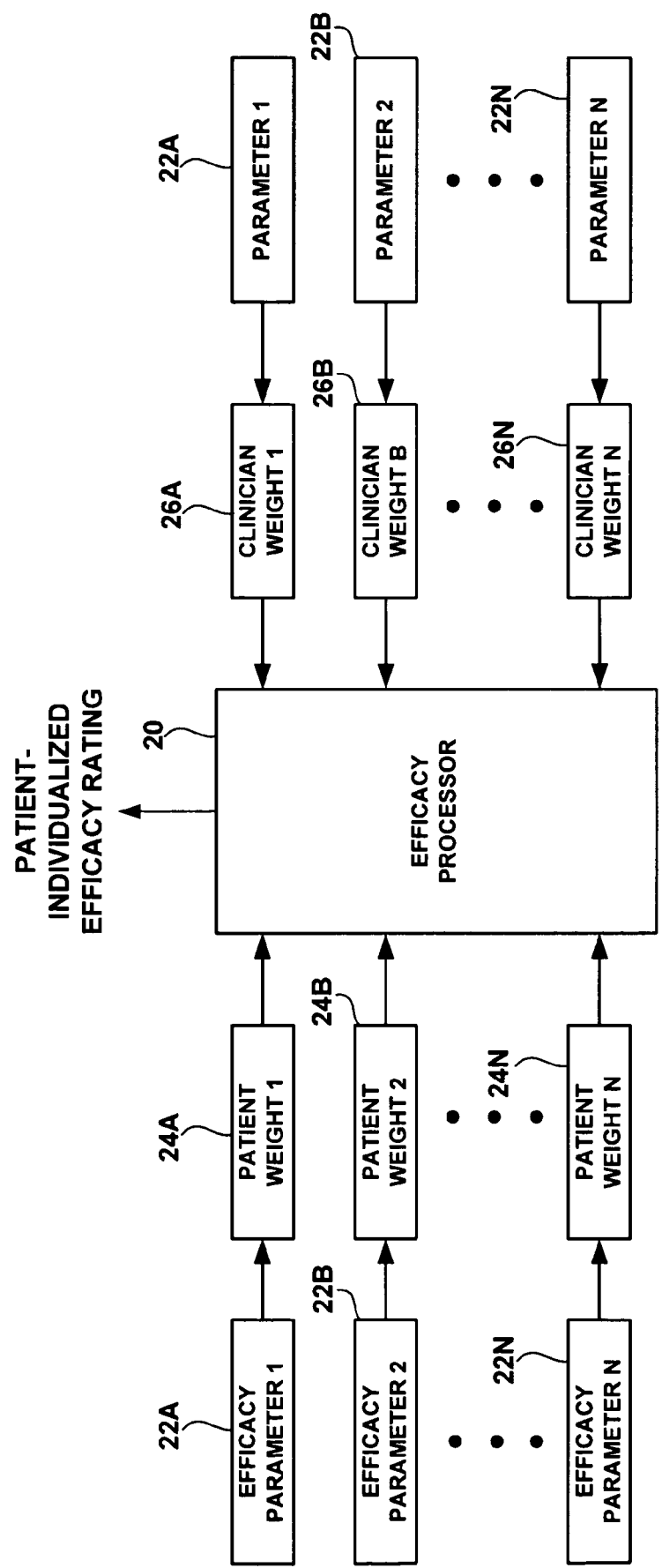
FIG. 2 is a block diagram illustrating generation of a patient-individualized efficacy rating.

FIG. 2 is a block diagram illustrating generation of a patient-individualized efficacy rating. The techniques illustrated in FIG. 2 may be implemented within clinician programmer 16, patient programmer 14, or both. In many embodiments, however, clinician programmer 16 will be configured to guide the clinician and/or patient through a process of patient-individualized efficacy rating. In general, an efficacy processor 20 computes a patient-individualized efficacy rating based on a list of efficacy parameters in combination with patient and/or clinician weighting values. The clinician and/or patient specifies a list of efficacy parameters 22A-22N that will be relevant in judging efficacy of programs designed to deliver a particular electrical stimulation therapy. For example, the selected efficacy parameters may pertain to those parameters useful in evaluating the efficacy of electrical stimulation for urinary incontinence therapy for a particular patient.

The list of efficacy parameters 22A-22N for a particular type of therapy may be fixed from patient to patient. Alternatively, a clinician and/or patient may select a subset of efficacy parameters from a larger list, e.g., based on perceived relevance of the parameters to the particular patient's condition or situation. Hence, different lists of efficacy parameters may be selected for different patients. As a further alternative, the clinician and patient may use different lists of efficacy parameters, which may be mutually exclusive or overlapping. For example, the patient list of parameters 22A-22N may include parameters subjectively evaluated by the patient, while the clinician list of parameters 22A-22N may include parameters objectively evaluated by the clinician. In a typical embodiment, however, the list of efficacy parameters 22A-22N may be identical for the patient and clinician.

As one example, a list of efficacy parameters 22A-22N for incontinence therapy may include incontinent episodes, urination frequency, and nocturia, as well as undesirable side effects such as pain, adverse sensory feeling such as parasthesia, and sexual dysfunction. In addition, in some embodiments, the efficacy parameters may include a quality of life (QOL) parameter defined according to a survey. Other parameters may include battery depletion rate, retention for urinary incontinence, and/or constipation for fecal incontinence.

A patient may select all or some of the parameters from the list based on the relevance of the parameters to the patient. Alternatively, the patient may select all of the parameters and weight them according to relevance. In either case, the patient specifies weighting values 24A-24N for each of the parameters. If a parameter is irrelevant, it may be omitted from the list or, more preferably, weighted with a very low or zero-value weighting value. Similarly, the clinician may specify weighting values 26A-26N for the parameters.

The patient-individualized efficacy rating may rely on patient weighting values 24A-24N only, clinician weighting values 26A-26N only, or a combination of the patient and clinician weighting values. In either case, efficacy processor 20 multiplies the respective efficacy parameter values by the respective weighting values, or applies some other mathematical function or lookup operation that applies the parameter values and weighting values, to produce the customized efficacy rating. The weighting values may be expressed in a variety of ways, and converted as appropriate to facilitate calculation.

For example, a patient may enter, for use as a weighting value, a numeric value such as a percentage (e.g., 0% for no relevance and 100% for high relevance), a ranking indicating relative priority (e.g., 1 for high relevance and n for low relevance), a symbol indicating relative priority (e.g., an exclamation point for high relevance and a dash for low relevance), a color indicating relative priority (e.g., red for high relevance and gray for low relevance), or any of a variety of alternative weighting value indicators. Notably, some of the weighting values for different parameters may have the same values. For example, parameter 22A and 22B may be assigned the same weighting values if they are considered equally relevant to the patient-individualized efficacy rating.

As an illustration, the list of parameter values 22A-22N may include nocturia, urination frequency and incontinent episodes. These parameter values may have positive or negative connotations. For example, the parameter values may be viewed in terms of the severity of nocturia, urination frequency or incontinent episodes, which has a negative connotation. Alternatively, the parameter values may be viewed in terms of efficacy of the therapy in preventing such problems, which has a positive connotation. In either case, the patient applies a weighting value that, in effect, prioritizes the parameters relative to one another.

The patient may consider incontinent episodes to be the highest priority for therapy, and may accept lesser efficacy for urination frequency and incontinent episodes. The lesser efficacy levels may be equal or different for urination frequency and incontinent episodes. For example, the patient may initially assign a weighting value of 70% to incontinent episodes, and weighting values of 40% to nocturia and urinary frequency. If the patient continues to suffer from incontinent episodes upon initiation of therapy, the patient may elect to increase the weighting value for incontinent episodes to 90% and either maintain or reduce the weighting values for nocturia and urination frequency.

In each case, the efficacy values for the respective parameters are multiplied by the weighting values to produce an overall patient-individualized efficacy rating. Hence, if efficacy is high for both nocturia and urination frequency, the overall patient-individualized efficacy rating will nevertheless reveal relatively low efficacy if the patient has weighted incontinent episodes highest, and continues to experience incontinent episodes. Conversely, even if efficacy is low for urination frequency and/or nocturia, the indication of overall patient-individualized efficacy may still be relatively high if the patient's primary concern, incontinent episodes, is adequately addressed.

By dividing efficacy into multiple parameters, and assigning appropriate weighting values to the parameters for each patient, efficacy processor 20 presents a customized view of efficacy for each patient. In this manner, efficacy processor 20 directly or indirectly takes into account differences between patients, such as patient age, gender, physiology, disease state, activity level, or activity profile. In particular, the patient's age, gender, activity level and activity profile, i.e., type of activities, may result in substantially different therapy priorities.

As an illustration, two different patients are considered. Patient 1 is employed as a sales person and must make several local sales calls per day. Often, access to restroom facilities may be inconvenient for Patient 1 as she meets with customers. In addition, Patient 1 is an avid golfer and leads a fairly active lifestyle. Patient 2 does not work outside the home and leads a relatively sedentary lifestyle.

For Patient 1, elimination of incontinent episodes is a primary objective due to possible interference with the patient's occupation and activity level. Urination frequency is an important but lesser concern for Patient 1. In this example, Patient 1 is not highly concerned about nocturia, which occurs at home. Instead, Patient 1 is more concerned with events during the day and away from the home. Accordingly, Patient 1 may apply a very high weighting value to incontinent episodes, a moderate weighting value to urination frequency, and a relatively low weighting value to nocturia.

Patient 2, on the contrary, seeks more even therapeutic improvement for both incontinent episodes and nocturia. With a sedentary, stay-at-home lifestyle, incontinent episodes are a significant concern for Patient 2, but not necessarily more than that associated with nocturia. With ready access to restroom facilities at home, Patient 2 may view urination frequency as less of a concern. Hence, Patient 2 may apply a relatively moderate to high weighting values to incontinent episodes and nocturia, but a low weighting level to urination frequency.

As further examples, it is assumed that at least some of the efficacy parameter values relate to undesirable side effects, such as pain, parasthesia or sexual dysfunction. Also, one or more parameter values may be objective measures of QOL obtained, e.g., as obtained manually or electronically from a patient survey. For Patient 1, parasthesia caused by electrical stimulation may be generally tolerable. However, Patient 1 may not be able to tolerate painful side effects during her daily routine. Patient 2 likewise may not tolerate pain well, but also rates parasthesia as highly undesirable. For sexual dysfunction, the objectives of Patients 1 and 2 may diverge greatly, particularly on the basis of age or relationship status. Accordingly, one patient may value avoidance of sexual dysfunction highly, while the other views avoidance of sexual dysfunction as a low priority.

As shown in FIG. 2, the weighting values specified by a patient may be accompanied or combined by weighting values specified by the clinician. Although a patient may provide a subjective prioritization of efficacy parameter values, the clinician may have a more objective view guided by more in-depth medical knowledge or experience. In this case, efficacy processor 20 may produce separate efficacy ratings for the patient and clinician, or a combined efficacy rating based on both the patient weighting values and the clinician weighting values. As a further embodiment, the patient weighting values and clinician weighting values could be weighted relative to one another. In this manner, the patient weighting values can be prioritized over the clinician weighting values, or vice versa, so that one of the two parties (patient and clinician) is given more importance in calculating the overall efficacy rating.

In general, the efficacy value is a function of the weighting value and the efficacy parameter values. For example, if a patient selects incontinent episodes, urination frequency and nocturia as parameters, and assigns weighting values of 70%, 40% and 40%, respectively, then respective efficacy parameter values of 50, 80 and 80 result in individual efficacy rating values of 35, 32 and 32. The sum of the efficacy rating values in this example is 99, which serves as the patient-individualized efficacy rating for the therapy delivered to the patient. The efficacy rating may be further modified by multiplying the resulting individual efficacy rating values by the respective clinician weighting values.

In either case, the ultimate patient-individualized efficacy rating can be compared to a one or more threshold values to determine whether efficacy is acceptable, or whether the therapy should be adjusted to improve the efficacy rating. The threshold values may be established and adjusted by a clinician, and formulated to represent values that represent overall therapeutic efficacy. In this manner, relative efficacy can be determined for a particular patient by comparing the patient-individualized efficacy rating to the threshold value or values.

Figure 3:
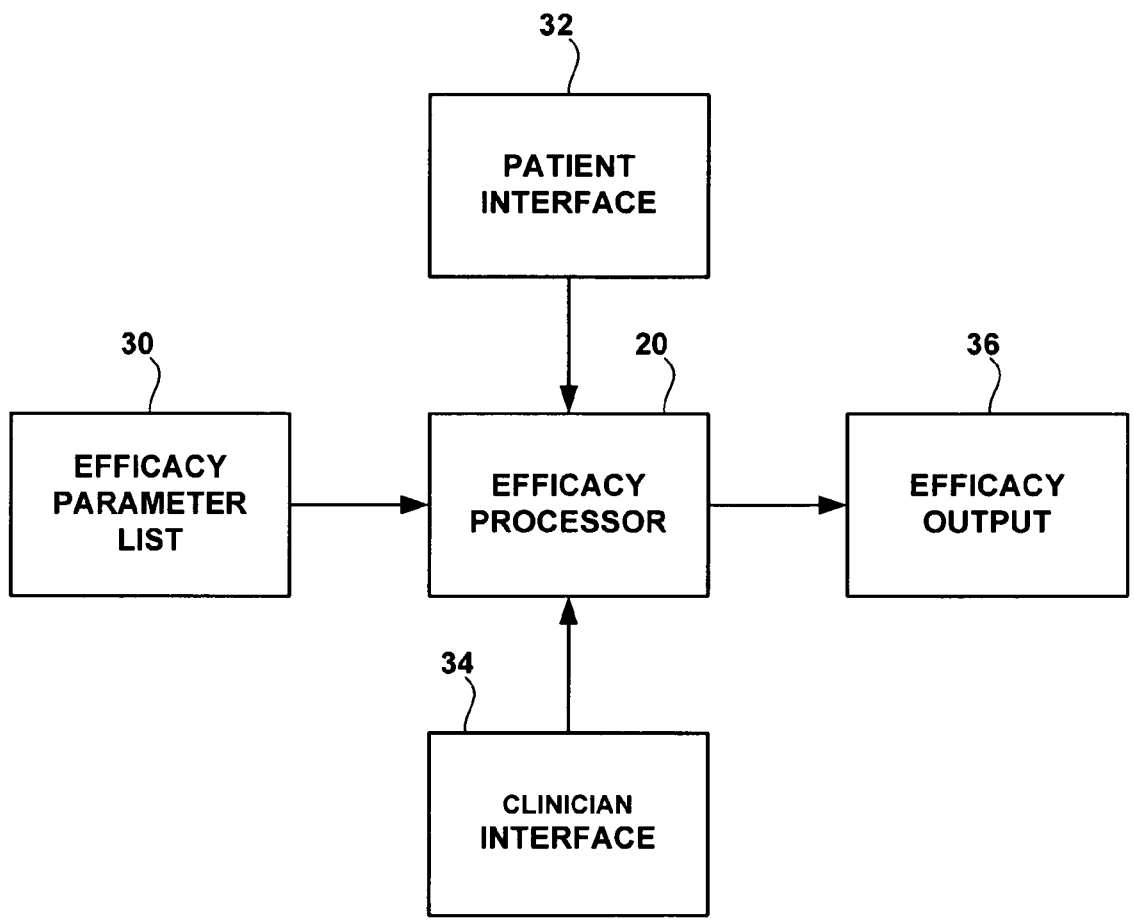
FIG. 3 is a block diagram illustrating a system for generating a patient-individualized efficacy rating.

FIG. 3 is a block diagram illustrating a system for generating a patient-individualized efficacy rating. As shown in FIG. 3, efficacy processor 20 accesses an efficacy parameter list 30 and presents it to a patient and/or clinician via patient interface 32 and clinician interface 34. The patient and clinician interfaces 32, 34 may be the same interface or different interfaces, and may include input media such as a keypad, buttons, touchscreen or the like, and output media such as a graphical display and audio output device.

For convenience, in the context of interaction with efficacy processor 20, a patient or clinician may be referred to as a user. Efficacy parameter list 30 includes a list of parameters for selection by the user via either of interface 32, 34. In some embodiments, the user may select a fixed list for particular therapy application such as electrical stimulation for urinary incontinence. Alternatively, the user may select a subset of the parameters in efficacy parameter list 30. As a further alternative, in some embodiments, a user may be permitted to add additional parameters to efficacy parameter list 30.

In addition to selection and/or specification of efficacy parameters, the user enters weighting values for the efficacy parameters via interface 32 or 34. Efficacy processor 20 may present each efficacy parameter from efficacy parameter list 30 with a default weighting value. The user may keep the default weighting value for some or all of the efficacy parameters, and may enter new weighting values for some or all of the efficacy parameters. The default weighting values may be established by a clinician based on objective weighting values obtained for a patient class at large. The individual weighting adjustments provided by the user modify the weighting values to support patient-individualized efficacy rating.

Using the efficacy parameter list selected or provided by the user, and the weighting values provided by the user, efficacy processor 20 produces efficacy output 36 in the form of a patient-individualized efficacy rating. In particular, upon application of electrical stimulation to the patient, efficacy processor 20 receives efficacy input for each of the efficacy parameters, e.g., via patient interface 32 and/or clinician interface 34. The efficacy input may take a variety of forms, including numeric values, rankings, symbolic selections, color selections, or the like. For example, the input may be entered into efficacy processor 20 by keying in information or selecting or manipulating media such as slider bars, radio buttons, and the like presented via a graphical display. Additionally, or in the alternative, some efficacy input may be obtained automatically, e.g., from sensors that obtain signals indicative of physiological conditions relating to efficacy.

Efficacy processor 20 computes the efficacy output 36 based on the efficacy parameters, the pertinent weighting values, and the efficacy rating input. The efficacy output 36 may be presented in a variety of ways, e.g., as a single numeric value, multiple numeric values ranking individual efficacy parameters, symbolic representations, color-based representations or the like. In addition, the efficacy output 36 may indicate whether the patient-individualized efficacy rating meets or exceeds an applicable threshold or thresholds, or other efficacy criteria.

Figure 4:
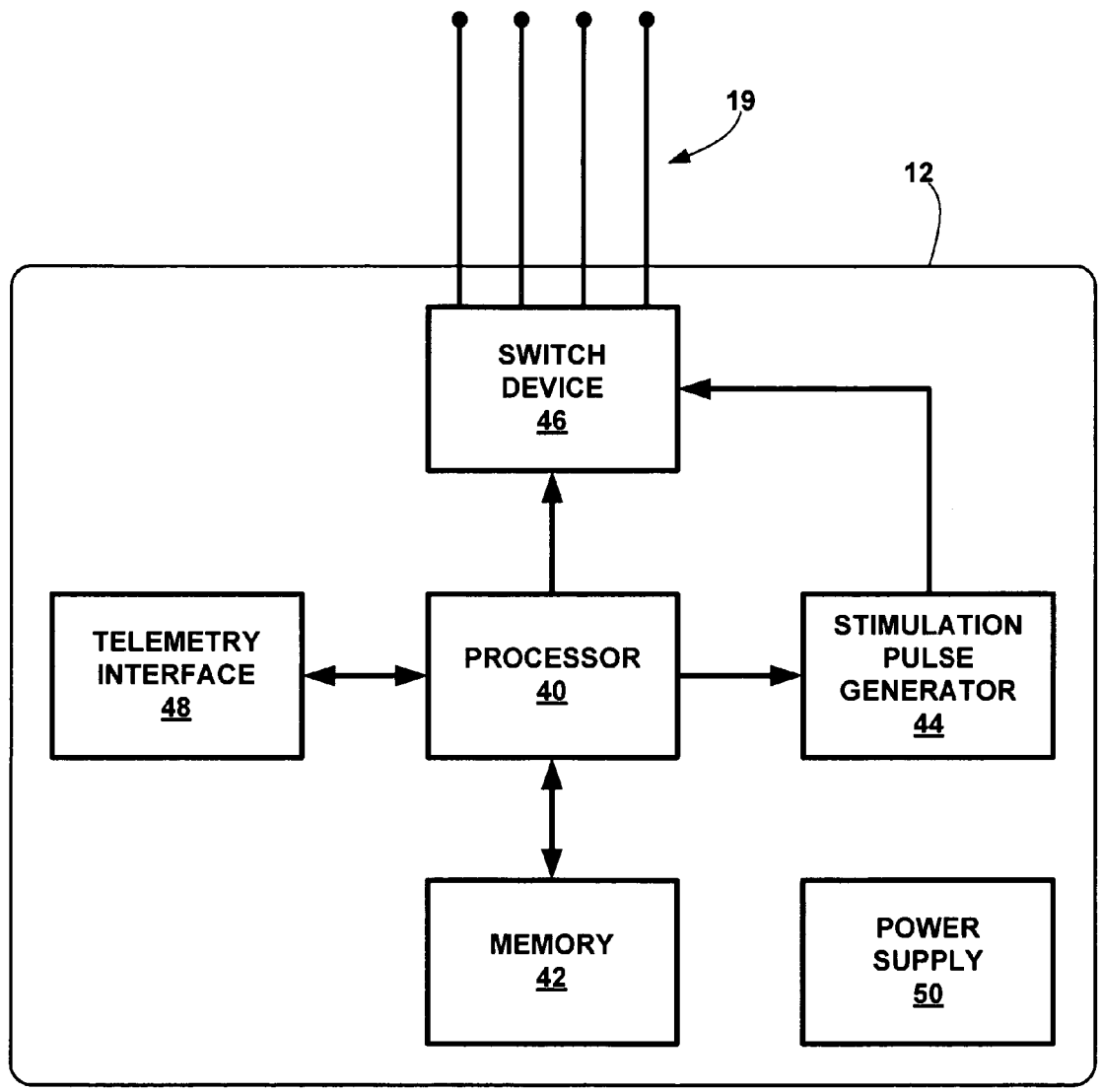
FIG. 4 is a block diagram illustrating an implantable electrical stimulator.

FIG. 4 is a block diagram illustrating an implantable electrical stimulator 12. In the example of FIG. 4, stimulator 12 includes a processor 40, memory 42, stimulation pulse generator 44, switch device 46, telemetry interface 48, and power supply 50. Memory 42 may store instructions for execution by processor 40 and stimulation therapy data. Memory 42 may include one or more memories for storing instructions and data. Processor 40 controls stimulation pulse generator 44 to generate electrical stimulation pulses according to a stimulation program specifying stimulation parameters, such as electrode combination, electrode polarity, voltage or current amplitude, pulse width and pulse rate. Processor 40 also controls switch device 46 to deliver electrical stimulation therapy via one or more selected electrodes 19.

In general, stimulator 12 may include a biocompatible housing with one or more biocompatible leads extending from the housing. One or more electrodes are carried on the leads, e.g., at a distal end of the leads. In addition, in some embodiments, the housing of stimulator 12 may serve as, or carry, one or more electrodes, e.g., for formulation of unipolar electrode combinations with electrodes carried by the leads. Stimulator 12 is implanted within patient 12, e.g., in a subcutaneous pocket within the abdomen or lower back. One or more leads 18 (not shown in FIG. 4) are tunneled from stimulator 12 through tissue to reach target tissue for delivery of stimulations pulses via electrodes 19. Electrodes 19 may be ring electrodes, planar paddle electrodes, cuff electrodes, conformable electrodes or any other type of electrodes capable of forming unipolar, bipolar or multipolar electrode combinations.

The target tissue may be any tissue affected by electrical pulses. Such tissue includes nerves, smooth muscle, and skeletal muscle. For urinary incontinence, as an example, the target tissue is one or more nerves of the pelvic floor, such as the sacral or pudendal nerves, which innervate the urinary sphincter or other muscles of the pelvic floor involved in the urinary system. The urinary sphincter aids in controlling urge and stress incontinence, and stimulation of a dysfunctional urinary sphincter may reduce or eliminate the condition of urinary incontinence.

Processor 40 controls stimulation pulse generator 44 to deliver electrical stimulation therapy via one or more electrodes 19. An exemplary range of electrical stimulation pulse parameters likely to be effective in treating urinary incontinence, e.g., when applied to the sacral or pudendal nerves, are as follows:

1. Frequency: between approximately 0.5 Hz and 500 Hz, more preferably between approximately 5 Hz and 250 Hz, and still more preferably between approximately 10 Hz and 50 Hz.

2. Amplitude: between approximately 0.1 volts and 50 volts, more preferably between approximately 0.5 volts and 20 volts, and still more preferably between approximately 1 volt and 10 volts.

3. Pulse Width: between about 10 microseconds and 5000 microseconds, more preferably between approximately 100 microseconds and 1000 microseconds, and still more preferably between approximately 180 microseconds and 450 microseconds.

A clinician modifies the stimulation parameters in response to efficacy output from efficacy processor 20. With this information, the clinician is able to monitor therapy efficacy and change the program parameters to more effectively treat patient 12. In particular, the stimulation parameters may be adjusted in order to improve pelvic floor tone or cause more effective constriction of the urinary sphincter and thereby avoid involuntary leakage. Also, in some cases, the stimulation parameters may be adjusted to reduce undesirable side effects.

Processor 40 controls telemetry circuit 48 to send and receive information. Wireless telemetry in stimulator 12 may be accomplished by radio frequency (RF) communication or proximal inductive interaction of neurostimulator 12 with external programmer 14, 16. Power supply 50 may be a rechargeable or non-rechargeable battery, or alternatively take the form of a transcutaneous inductive power interface. In some embodiments, efficacy of particular stimulation parameters may be evaluated in terms of power conservation. In particular, efficacy may be judged in part by the rate at which the parameters tend to drain power supply 50.

Figure 5:
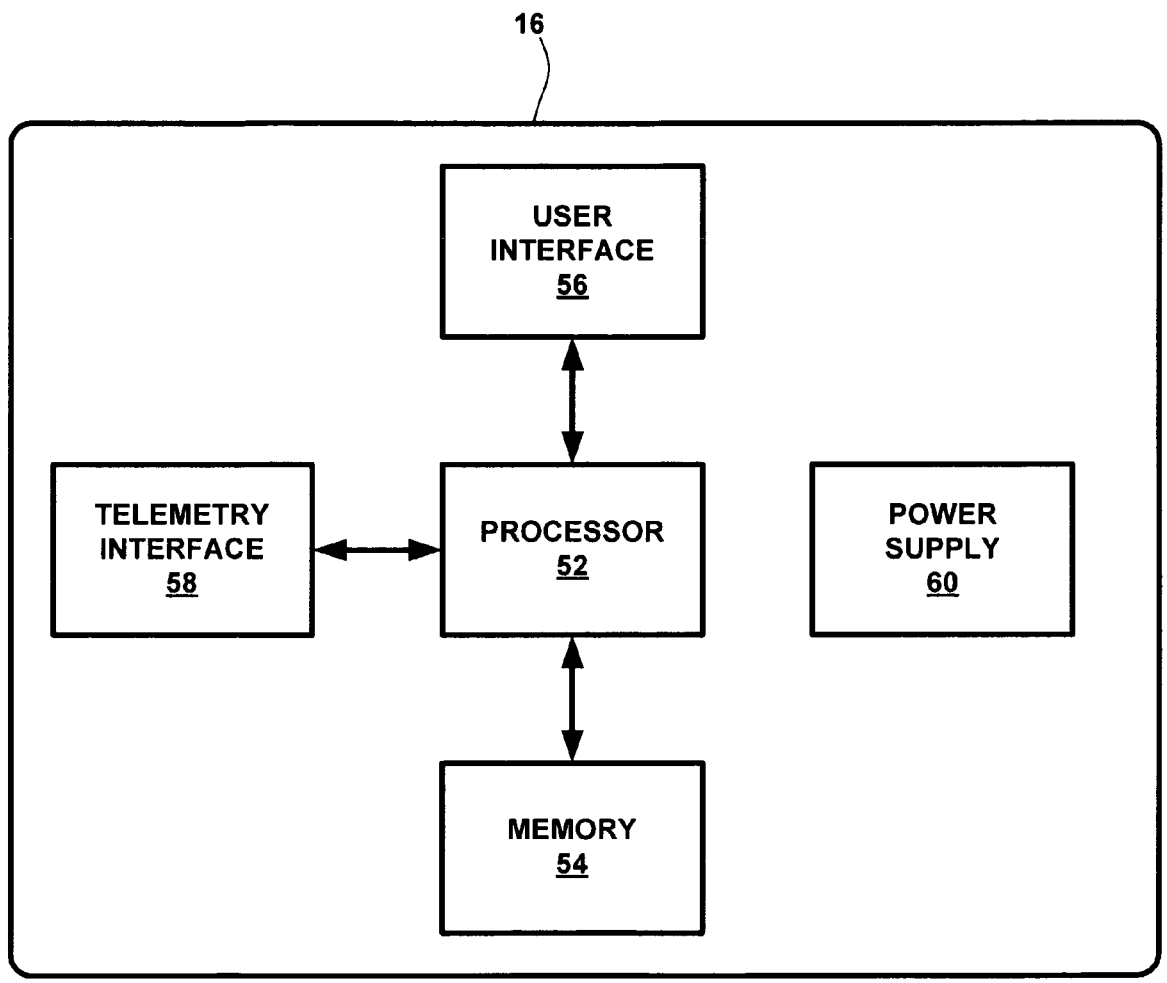
FIG. 5 is a block diagram illustrating an external programmer for the implantable stimulator of FIG. 4.

FIG. 5 is a functional block diagram illustrating various components of an external programmer 16. External programmer 16 is shown as the clinician programmer of FIG. 1. However, the components in FIG. 5 also may be provided in a patient programmer 14. Programmer 16 communicates wirelessly with implantable stimulator 12, e.g., to program the stimulator to deliver particular stimulation programs or to adjust stimulation parameters. Also, programmer 16 provides a platform for patient-individualized efficacy rating. As shown in FIG. 5, external programmer 24 includes processor 52, memory 54, user interface 56, telemetry interface 58 and power supply 60. A clinician or patient interacts with user interface 56 in order to manually select different stimulation programs, adjust stimulation parameters (e.g., amplitude, pulse width, pulse rate), select efficacy parameters, select and change weighting values for efficacy parameters, and view efficacy ratings.

User interface 56 may include a screen and one or more input media that allow external programmer 16 to receive input from a user. The screen may be a liquid crystal display (LCD). Input media may include a touch screen, buttons, a scroll wheel, a mouse, trackball, or other input media. Processor 52 controls user interface 56 to receive information from a user and present information to a user. In addition, the functionality of efficacy processor 20 (FIGS. 2 and 3) may be provided within processor 52, in addition to other functionality. Processor 52 retrieves data from memory 54 and stores data within the memory. Processor 52 also controls the transmission of data through telemetry circuit 58 to and from stimulator 12. In some embodiments, programmer 16 may communicate with other devices. For example, a patient programmer 14 may communicate with a clinician programmer 16 via wired or wireless media.

When used by a patient, the programmer may be a small, battery-powered, portable device that accompanies the patient throughout a daily routine. For a clinician, the programmer also may be a small, battery-powered portable device. Alternatively, the programmer may take the form of a tablet, notebook, desktop computer or a computer workstation. For in-clinic use, the programmer may be equipped with a larger display to facilitate viewing of efficacy rating information. In particular, efficacy visualization in accordance with this disclosure may involve presentation of detailed graphs or other graphical information that may be more appropriately displayed on a larger display, such as a flat panel monitor, e.g., from seven inches to twenty inches in diagonal dimension.

Figure 6:
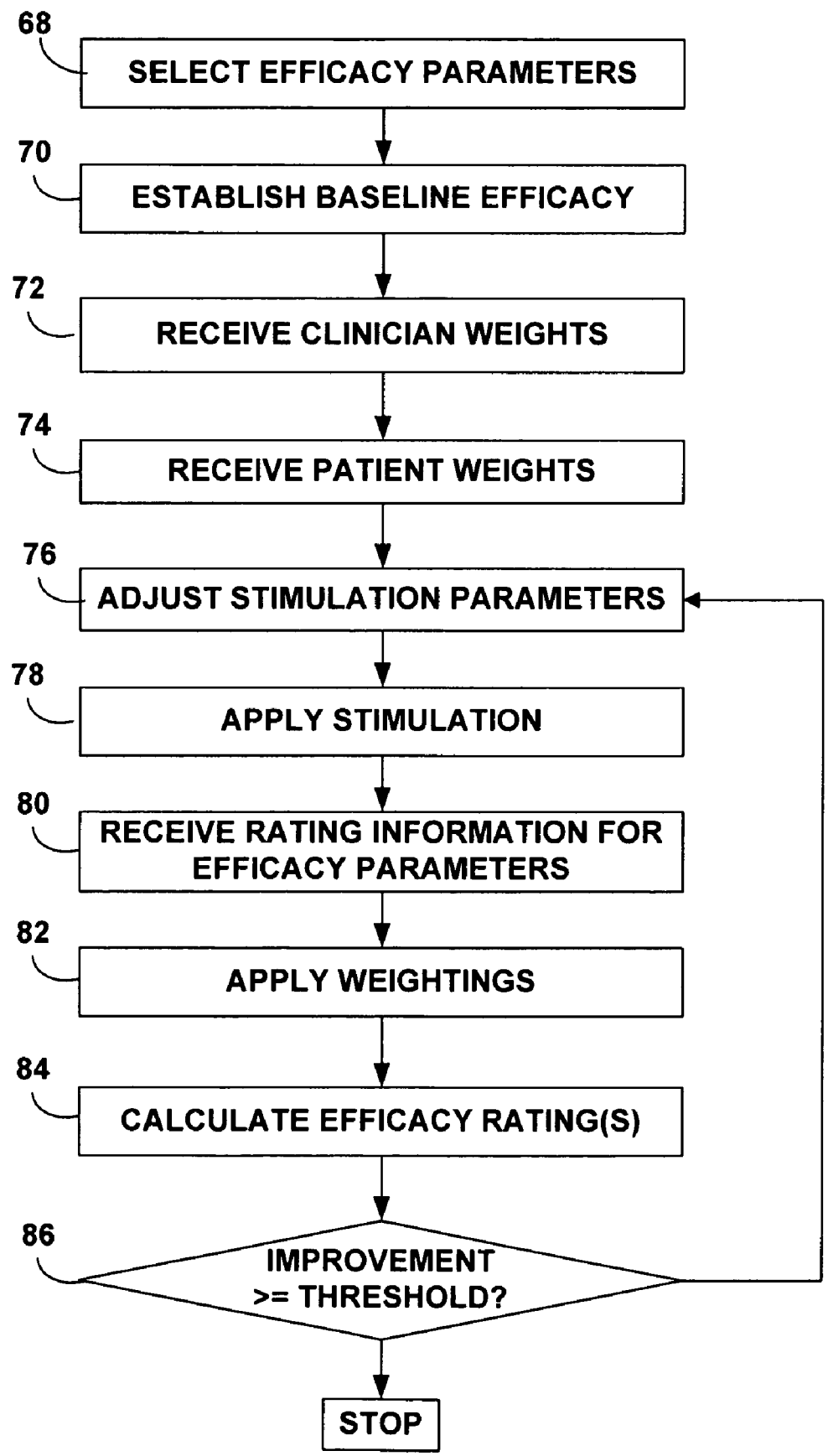
FIG. 6 is a flow diagram illustrating a process for generating a patient-individualized efficacy rating.

FIG. 6 is a flow diagram illustrating a process for generating a patient-individualized efficacy rating. The process shown in FIG. 6 may be performed by a programmer, such as a patient programmer or clinician programmer, to capture and present individualized patient efficacy information. As shown in FIG. 6, for example, processor 52 of programmer 16 selects a set of efficacy parameters (68). Again, the efficacy parameters may be a fixed set of parameters, a subset of a larger set of efficacy parameters as selected by a user, or a set of efficacy parameters including all or a subset of a fixed set of parameters plus additional parameters entered by a user. Also, in some cases, the efficacy parameters may be at least partially dependent on sensors that are available (or practical for use with the patient) to gauge efficacy.

Processor 52 next establishes a baseline efficacy for the selected efficacy parameters (70). In particular, processor 52 accepts input from the user, patient and/or clinician, providing rating values for each of the selected efficacy parameters prior to application of electrical stimulation therapy. Alternatively, the baseline efficacy may be derived from a ratings obtained for a larger set of efficacy parameters at an earlier time, e.g., upon on initial evaluation of the patient. In either case, the baseline efficacy rating represents the patient's natural condition without the benefit of stimulation therapy. If the patient experiences three incontinent episodes per day and very frequency urination urges, this condition is reflected in the baseline efficacy rating. The baseline efficacy rating for each efficacy parameter may be rated in the same manner as post-stimulation efficacy. As an option for the user, however, the baseline efficacy ratings may be expressed as raw ratings or weighted efficacy ratings.

Processor 52 receives clinician weights (72) and patient weights (74) for each of the selected efficacy parameters. Although both clinician weights and patient weights are shown in the example of FIG. 6, in some embodiments, only one type of weight may be obtained. For example, the patient-individualized efficacy rating may rely on only the patient weight in some cases. Accordingly, obtaining both clinician weights and patient weights may be optional. Although weights are obtained after establishing baseline efficacy in the example of FIG. 6, the weights may be obtained at the same time the user selects efficacy parameters 68. Accordingly, in general, the order expressed in the flow diagram of FIG. 6 should not necessarily be considered limiting as to the order of operations in the process.

To prepare stimulation therapy, processor 52 sets and adjusts one or more stimulation parameters (76), such as electrode combination, electrode polarity, voltage or current amplitude, pulse width and pulse rate, either automatically or based on input from the user (patient or clinician). Upon application of stimulation (78), processor 52 receives rating information for the selected efficacy parameters (80). The efficacy parameters may be obtained from a user, such as clinician or patient, and/or from a sensor that obtains physiological information indicative of efficacy. In a urinary incontinence application, for example, a sensor may provide wetness information or bladder function information, such as contractile activity, pressure, flow or the like. Collected data may include acute events or evens obtained over time, e.g., such as voiding events or number of voiding events in a particular time period such s 24 hours.

Processor 52 applies the weighting values to the receiving rating information for the pertinent parameters (82). Again, the efficacy parameter values and weightings may be expressed as numeric values, or other symbolic or graphic indicia. However, processor 52 ordinarily will convert the efficacy parameter values and weightings to numeric values, if not already in numeric form, and calculate one or more efficacy ratings (84). The efficacy ratings preferably will include an overall efficacy rating that combines the weighted efficacy parameter values to give an indication of overall efficacy of the electrical stimulation therapy in alleviating the patient's condition or symptoms.

If the improvement in the patient's condition or symptoms, i.e., therapeutic efficacy relative to the baseline efficacy, meets or exceeds an application threshold (86), the therapy may be deemed acceptable and the process may stop, at least temporarily until efficacy is evaluated at a later time. Alternatively, if the improvement indicated by the efficacy rating does not meet or exceed the threshold (86), the process returns to the adjustment of stimulation parameters (76) and efficacy evaluation (78, 80, 82, 84, 86) in an effort to achieve acceptable efficacy. In either case, the efficacy rating is a patient-individualized efficacy rating that tailors the efficacy evaluation to the individual condition and/or desires of the particular patient. The process may continue on an iterative basis until acceptable efficacy is achieved, or the process is otherwise terminated by a user. Alternatively, the process may continue for an indefinite period, e.g., to fine tune the efficacy parameters.

Figure 7:
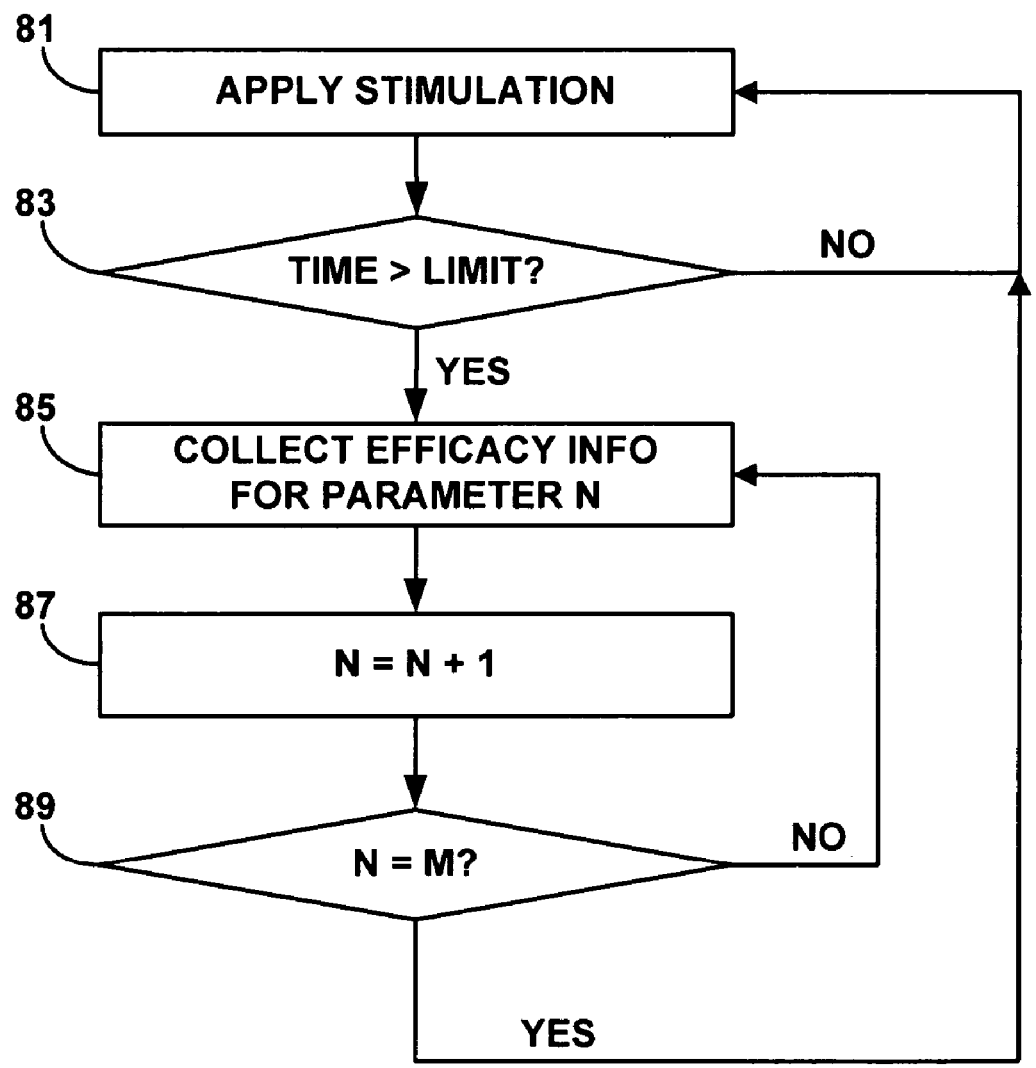
FIG. 7 is a flow diagram illustrating a process for collecting efficacy information.

FIG. 7 is a flow diagram illustrating a process for collecting efficacy information. In general, efficacy information may be collected immediately following or during application of stimulation to the patient. In many cases, however, it may be desirable to permit stimulation to be delivered for a period of minutes, hours or days before efficacy information is obtained. For example, some therapies and conditions may require several days of use before efficacy can be judged in a meaningful way. Accordingly, efficacy ratings may be obtained from the patient and/or clinician in the clinic during application of stimulation therapy. Alternatively, efficacy ratings may be obtained over an extended period of time, including times when the patient is outside of the clinic. In some cases, for urinary incontinence, information may be obtained in conjunction with a voiding diary that tracks voiding events by the patient.

For example, a patient programmer 14 may be equipped to elicit and accept user input specifying efficacy ratings at scheduled intervals. In some embodiments, efficacy ratings may be obtained when the patient makes an adjustment to a stimulation parameter, such as amplitude, pulse width or pulse rate. When the patient increases or decreases stimulation amplitude, for example, the programmer 14 may request that the patient enter efficacy rating information for one or more efficacy parameters. A decrease in stimulation amplitude or other parameters affecting stimulation intensity may indicate that the patient has experienced pain or discomfort.

As a further alternative, programmer 14 may be configured to derive efficacy rating information from patient information. If a patient repeatedly increases stimulation pulse rate, for example, programmer 14 may infer that the original parameter values did not yield acceptable efficacy for the patient. In this case, programmer 14 may reduce the efficacy rating for some or all efficacy parameters by a fixed amount or in proportion to the number or magnitude of the adjustments made by the patient.

The flowchart shown in FIG. 7 represents a general process for obtaining efficacy information from a user such as a patient over an extended period of time. As shown in FIG. 7, upon application of stimulation 81, a processor in programmer 14 determines whether a particular amount of time has elapsed, i.e., whether the elapsed time is greater than a time limit for eliciting efficacy feedback from the patient (83). If the time is greater than the limit (83), programmer 14 collects efficacy information for one of the efficacy parameters (85).

The process increments to obtain efficacy information for each of the efficacy parameters (87, 89, 85), until information is collected for all M selected efficacy parameters. At that point, the process returns to apply stimulation (81), and wait until the elapsed time exceeds the limit (83). Although application of stimulation (81) is shown as an operation in the process of FIG. 7, stimulation may be applied continuously or periodically according to a stimulation program, and need not stop while efficacy information is collected. The efficacy rating information, once collected, may be processed within patient programmer 14 or communicated to patient programmer 16 for calculation and presentation of a patient-individualized efficacy rating. Efficacy rating information may be obtained periodically, i.e., on a time-based schedule, or in an event-based manner in response to particular events, such as activation of therapy or adjustment of therapy parameters by the patient.

Figure 8:
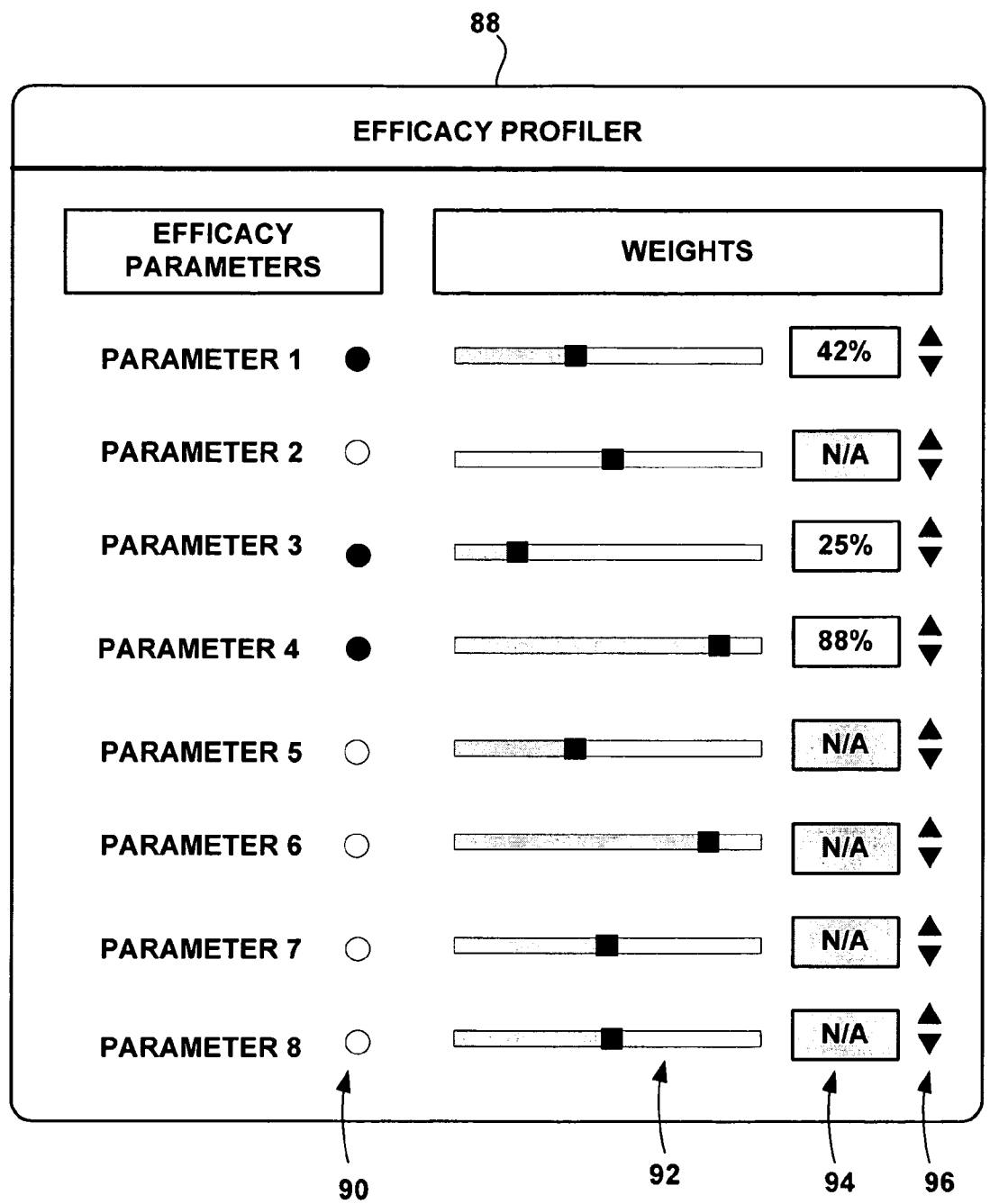
FIGS. 8 and 9 are diagrams of a user interface for selecting efficacy parameters and weighting values to profile efficacy for a patient.
Figure 9:
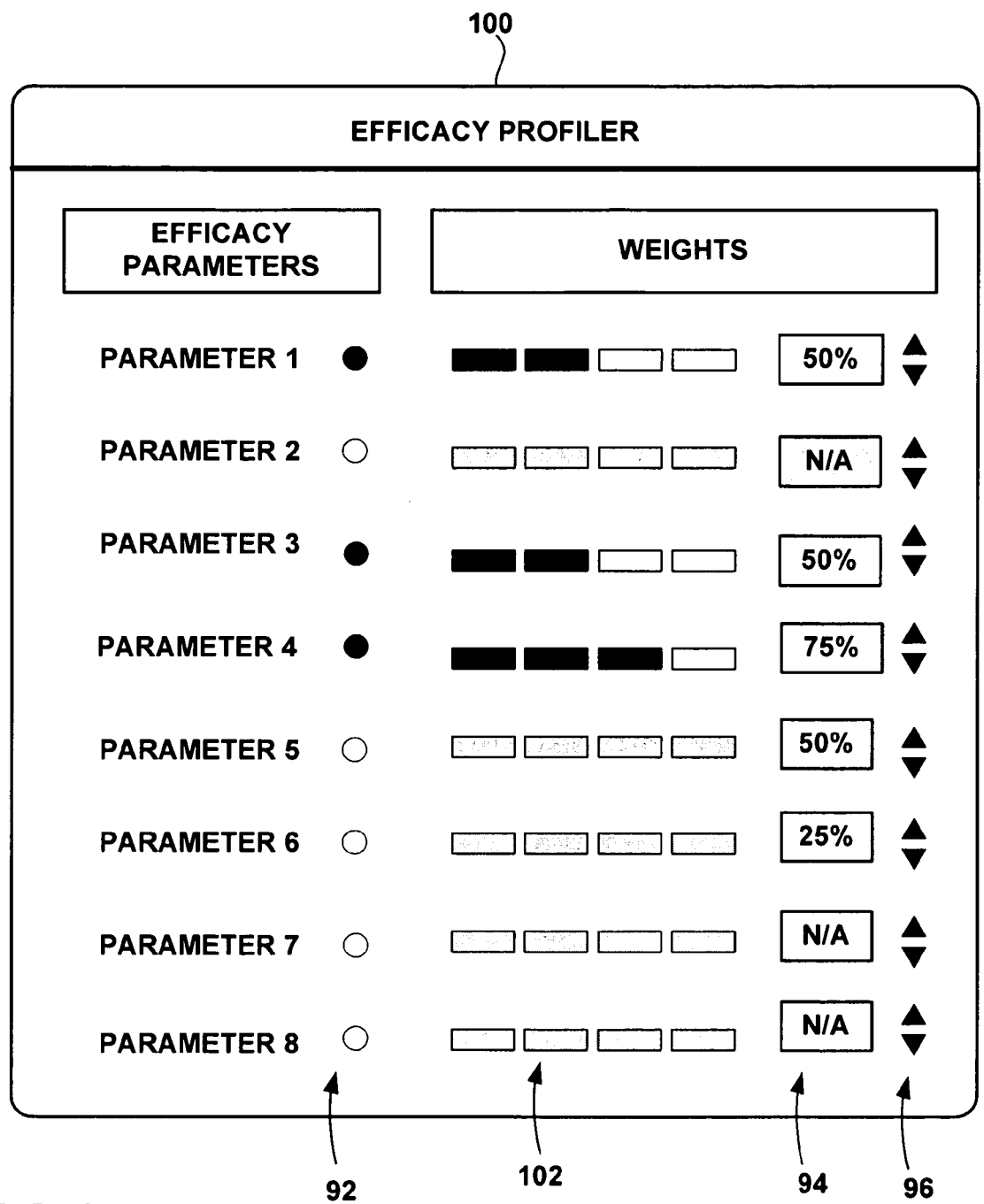

FIGS. 8 and 9 are diagrams of an exemplary user interface for selecting efficacy parameters and weighting values to profile efficacy for a patient. The user interface may be presented by patient programmer 14 or clinician programmer 16. As shown in FIG. 8, the efficacy profiler user interface permits a user (patient and/or clinician) to select efficacy parameters from a list of parameters. For example, the user may click on a checkbox or radio button 90 to select individual parameters from the list of efficacy parameters. In some embodiments, a user may be required to select a minimum number of efficacy parameters. Also, in some embodiments, a user may be required to select no more than a maximum number of efficacy parameters. The process of FIGS. 8 and 9 may be generally referred to as efficacy profiling in that it permits the user to customize a list of efficacy parameters for a particular patient, thereby profiling the efficacy to the patient.

In the example of FIGS. 8 and 9, programmer 14 or 16 presents eight different efficacy parameters for selection by a user. As an illustration, for a urinary incontinence application, the efficacy parameters may include incontinent episodes, urination frequency, nocturia, undesirable parasthesia, pain, retention, sexual dysfunction, and battery consumption rate. In some embodiments, the user may be permitted to add one or more efficacy parameters, beyond the list of parameters initially presented for selection. In this manner, customization of the parameter list may even include custom parameters created for a given patient. For each parameter, the user specifies a weighting value to indicate the relative importance of the efficacy parameter in the overall efficacy rating on a patient-individualized basis.

As shown in FIG. 8, the user may set the weighting values using a slider bar 92 and/or up-down arrows 96. In the example of FIG. 9, the user may set the weight value by clicking to select and deselect segments in a horizontal bar 102. In either case, the value of the weight is shown in a text box 94 horizontally aligned with the pertinent parameter. The value in box 94 may change according to the manipulation of the pertinent bar 92, 102 or up/down arrows 96. In addition, in some embodiments, the user may directly enter numeric information into the text boxes 94. Weighting information for non-selected parameters may be grayed out, or otherwise indicated to be inactive, e.g., with a not applicable "N/A" designation. A variety of different input media, such as arrows, sliders, bars, scroll inputs, and the like may be provided to increase or decrease the weights. Although a horizontal orientation of the parameters in rows is shown in the example of FIGS. 8 and 9, a vertical orientation or other orientations may be used. Illustration of numeric values as percentages is for purposes of example.

Figure 10:
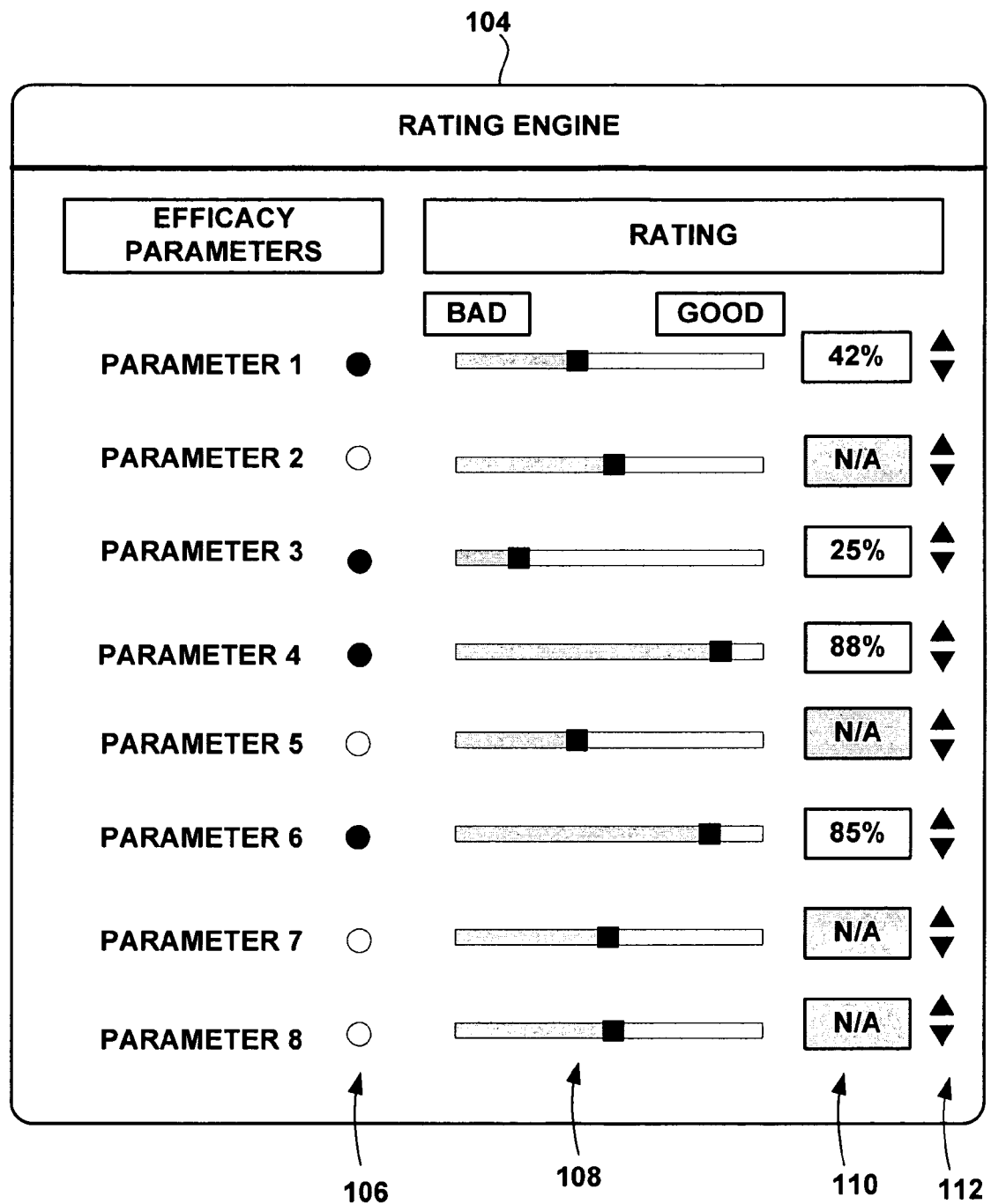
FIGS. 10 and 11 are diagrams of a user interface for recording efficacy parameter values.
Figure 11:
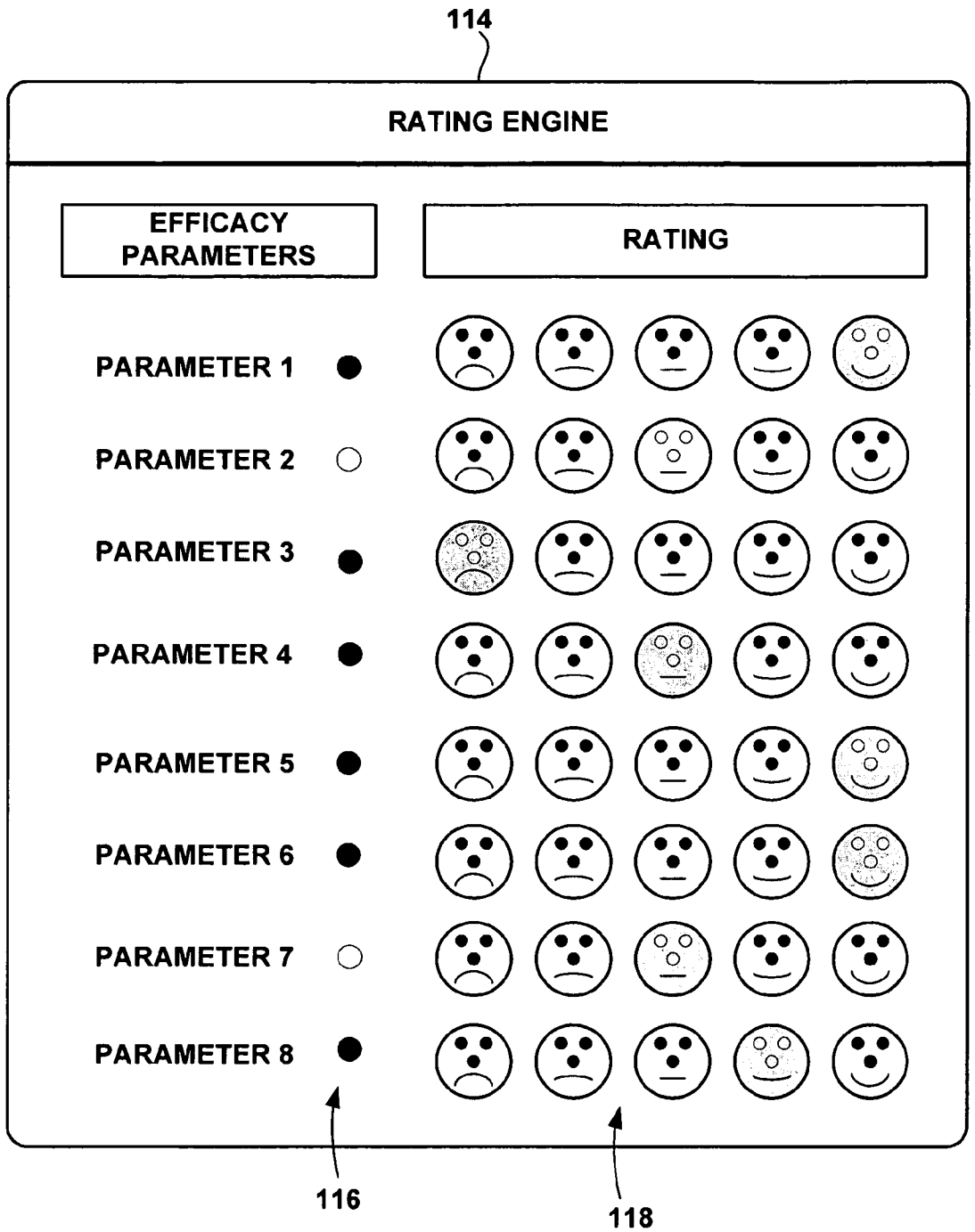

FIGS. 10 and 11 are diagrams of a user interface for recording efficacy parameter values. Once the efficacy profiling process is complete, e.g., as shown in FIGS. 8 and 9, programmer 14 or 16, as applicable, may present a rating engine user interface. The rating engine user interface may be used to collect information relating to selected efficacy parameters for both baseline and post-stimulation efficacy rating. The rating engine user interface may show all efficacy parameters in the original list presented to the user, or only those efficacy parameters that have been selected by the user. The selected parameters may be indicated, in part, by checkboxes or radio buttons 106. In either case, rating information can be entered for the selected efficacy parameters in a manner similar to setting the parameter weighing values, as shown in FIGS. 8 and 9.

In the example of FIG. 10, the user may use a slider bar 108 or up/down arrows 112. The rating value may be presented in a text box 110 that change according to the pertinent manipulation of the slider bar 108 and up/down arrows 112. In addition, in some embodiments, the user may directly enter numeric information into the text boxes 110. The scale along the length of slider bar 108 may include an indication or "bad" and "good" efficacy from left to right in order to orient the user. As in the example of FIG. 9, a set of clickable segments or other input media can be provided instead or, or in addition to slider bars 108. Once again, the user interface may have a horizontal or vertical orientation.

Instead of a numeric input, the rating engine user interface in FIG. 11 presents graphical symbols that correlate to good or bad efficacy. For example, in FIG. 11, each parameter in the list is horizontally aligned in a row with a set of faces, ranging from a frowning face at the left, and a neutral face in the middle, to smiling face at the right. In this case, efficacy extends from bad at the left to good at the right. In operation, the user clicks on one of the faces that best represents the efficacy presented by the pertinent efficacy parameter. Programmer 14 or 16 converts the selected face to a numeric representation for calculation of an overall efficacy rating, in conjunction with the weighting values entered previously by the patient and/or the clinician. As alternatives to graphical symbols such as faces, other graphical input media may be used such as colors or symbols.

Figure 12:
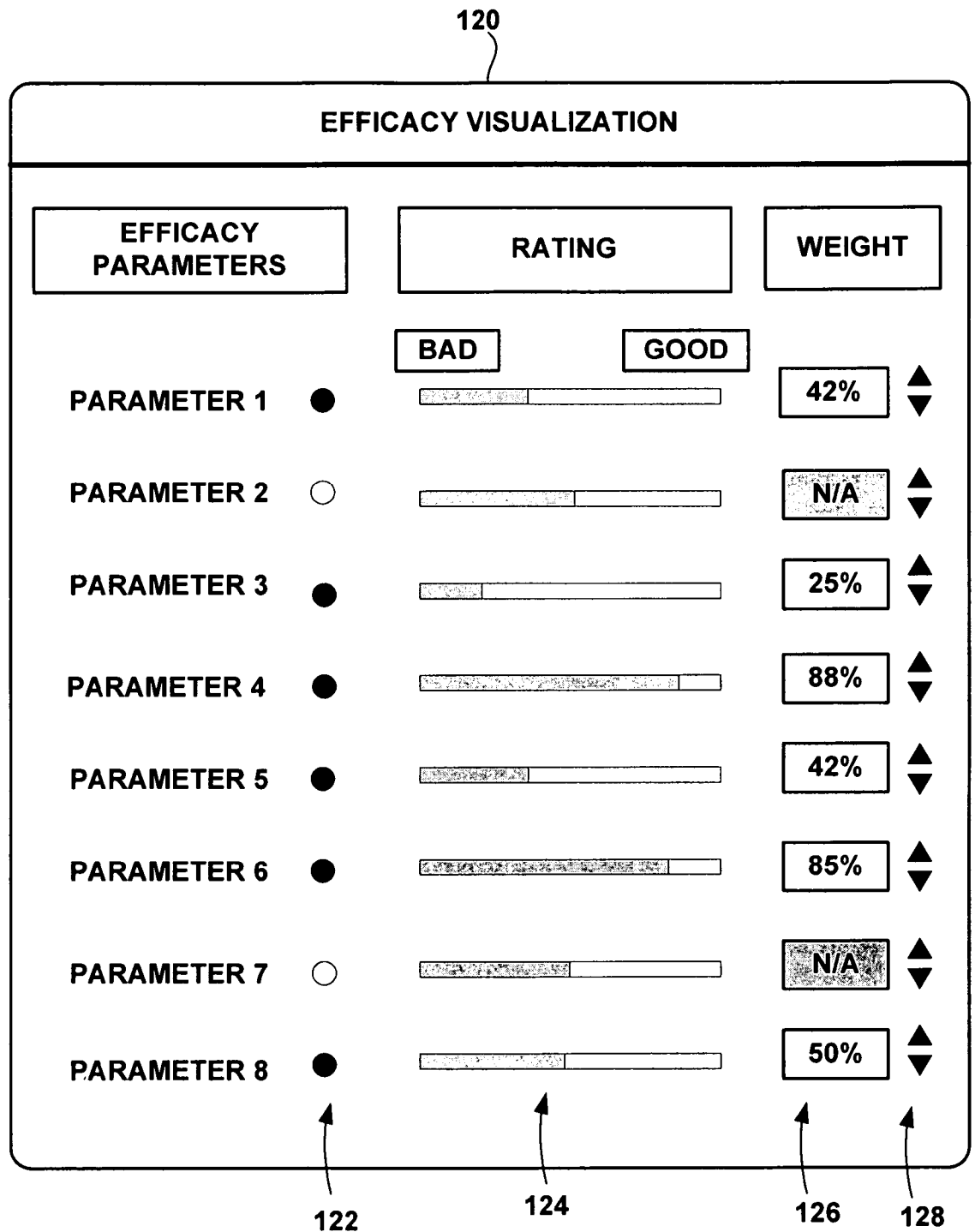
FIG. 12 is a diagram of a user interface for presenting a visualization of efficacy ratings.

FIG. 12 is a diagram of a user interface for presenting a visualization of efficacy ratings. In addition to providing a patient-individualized efficacy rating, it is useful for the patient and/or clinician to be able to visualize the efficacy rating graphically. For example, a graphical representation opens many opportunities for efficient modeling and adjustment of efficacy by adjusting stimulation parameters. For example, as will be described, a multi-axis graphical representation may be used to define a target or zone for adjustment and steering of electrical stimulation parameters. In particular, a clinician may adjust electrical stimulation parameters, with the aid of the efficacy visualization, to drive an overall efficacy value toward a target efficacy value.

Once a per-parameter and overall efficacy score have been determined, the data can be displayed to the user. Many different types of presentations may be provided. As examples, the efficacy visualization may present both per-parameter efficacy performance (e.g. along an axis) as well as overall efficacy performance (e.g., as a shaded area under a curve or within an object). Other examples may include presentation of variation in the overall or a particular efficacy score. Still other examples may include presentation of changes in efficacy parameter values over time, including simultaneous display of multiple sets of efficacy parameter values obtained at different evaluation times in the same display or display window, or different displays or display windows.

In the user interface of FIG. 12, the user selects the parameters to be presented. In addition, the user may adjust weightings for the parameters to change the shape of an efficacy parameter curve or object defined by the parameter values. In other words, the user may specify the weighting values for efficacy rating calculation, but also adjust the ratings, if desired, during visualization of the efficacy rating information. In some embodiments, an efficacy parameter value may be displayed in relation to a baseline efficacy parameter value, indicating the patient's original condition prior to stimulation, and a target efficacy parameter value, indicating a desired condition for the patient upon application of stimulation.

Figure 13:
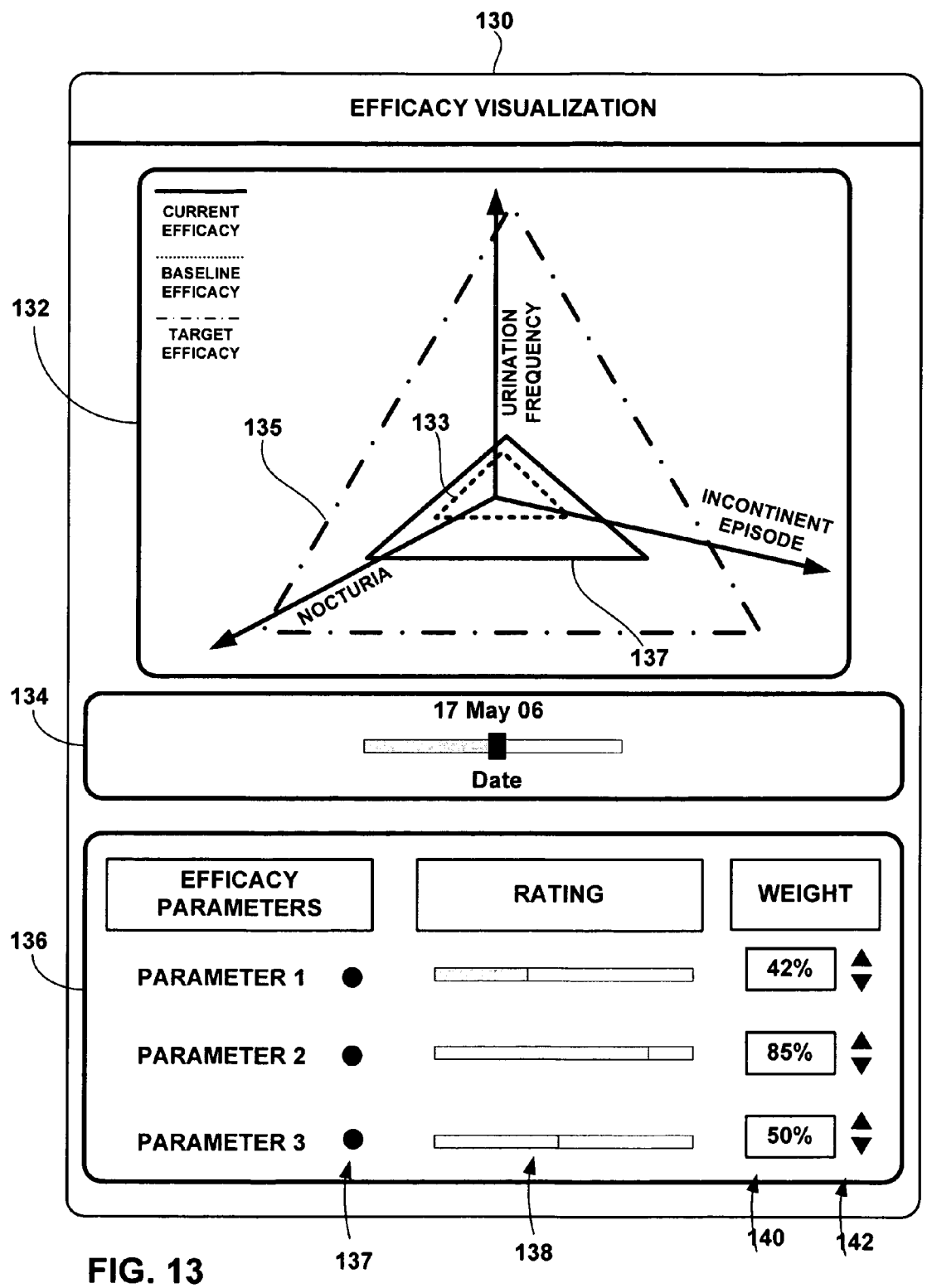
FIG. 13 is a diagram of a user interface for presenting a multi-axis visualization of efficacy ratings.

FIG. 13 is a diagram of a user interface 130 for presenting a multi-axis visualization of efficacy ratings. User interface 130 may be presented by programmer 14 or programmer 16. As shown in FIG. 13, user interface 130 presents a graphic display area 132, a date adjustment interface 134, and efficacy parameter adjustment interface 136. The efficacy parameter adjustment interface 136 permits a user to select efficacy parameters for presentation in graphic display area 132, e.g., using checkboxes or radio buttons 137. In addition, efficacy parameter adjustment interface 136 may permit the user to adjust efficacy ratings for the parameters, e.g., using slider bars 138, and adjust the weightings applied to the efficacy parameter rating values, e.g., using text entry boxes 140 and/or up/down arrows 142.

Graphic display area 132 presents a multi-axis representation of the efficacy parameters. In the example of FIG. 13, graphic display area 132 displays values for three different efficacy parameters along three different coordinate axes. In addition, graphic display area 132 interconnects the axis coordinates to create a shape. In the three-axis example of FIG. 13, interconnection of the three axis coordinates produces a triangle. As an example, the three different coordinate axes could indicate values for efficacy parameters relating to urinary incontinence therapy, such as frequency of incontinent episodes, urination frequency and nocturia, as shown in FIG. 13. However, the number and type of parameter selected for presentation in graphic display area 132 may vary. Moreover, user interface 130 may be adapted for a variety of different stimulation applications, and is not limited to urinary incontinence therapy. In the example of FIG. 13, the larger the triangle, or the higher the individual value on a coordinate axis, the higher is the efficacy rating.

In FIG. 13, an inner triangle 133 represents baseline efficacy values for the selected stimulation parameters. An outer triangle 135 represents target efficacy values for the selected stimulation parameters. Hence, ideally, electrical stimulation would drive the therapy efficacy values from baseline triangle 133 to target triangle 135. As a practical matter, it is desirable that electrical stimulation at least move efficacy values from baseline triangle 133 toward target triangle 135. Triangle 137 represents actual efficacy, and shows an improvement upon application of stimulation therapy to the patient. Notably, the shape of triangles 133, 135, 137 will vary according to the individual efficacy parameter values and associated weighting values.

Date adjustment area 134 includes a slider bar that permits a user to adjust the date for which efficacy parameter values are presented in display area 132. A programmer 14 or 16 may be used to obtain multiple sets of efficacy parameter values from the user at different times or on different dates. Programmer 14 or 16 also may be configured to obtain multiple sets of efficacy parameter values corresponding to different stimulation parameter sets, such as different stimulation programs. In this manner, the different sets of data displayed in display area may correspond to different dates and/or different stimulation parameters.

In either case, multiple sets of efficacy parameter values can be stored so that a user can retrieve them for presentation and analysis. In this manner, a user can evaluate progress or trends in the stimulation efficacy over an extended period of time, or analyze the effects of different parameter sets. As the user adjusts the slider bar in date adjustment area 134 to change the pertinent date, programmer 14 or 16 retrieves different efficacy parameter value sets corresponding to each date, and uses the retrieved information to modify the graphical presentation in area 132. Similarly, a slider bar, dropdown menu or the like may be provided to permit the user to select different parameter sets that have been applied and evaluated.

As the user changes the date, the shape of triangle 137 changes according to the efficacy parameter values that correspond to the date. In this manner, the user may observe the current efficacy triangle (for the given date) extend outward from the baseline efficacy triangle 133 and toward the target efficacy triangle 135, providing a useful progressive view of the therapy. In some embodiments, programmer 14 or 16 may provide an auto-tracking feature that progressively moves triangle 137 between a starting date and an ending date, without the need for the user to manually adjust the date.

In addition to the features shown in FIG. 13, user interface 130 may include other features. For example, user interface 130 may present a button that permits the user to view current electrical stimulation parameters associated with the current efficacy value, or historical electrical stimulation parameters associated with past current efficacy values, or projected electrical stimulation parameters associated with a target efficacy value. Other buttons may permit access to a screen that permits modification of the stimulation parameters.

In addition, parameter adjustment interface 136 may be normally hidden but viewable by clicking on a button that reveals the parameter adjustment interface so that the user can adjust weighting values, and hence prioritization of efficacy parameters. Also, in some embodiments, programmer 14 or 16 may recommend a best set of stimulation parameters that correlate to a best set of efficacy parameter values, and permit the user to find and accept this best set of stimulation parameters for stimulator 12.

Figure 14:
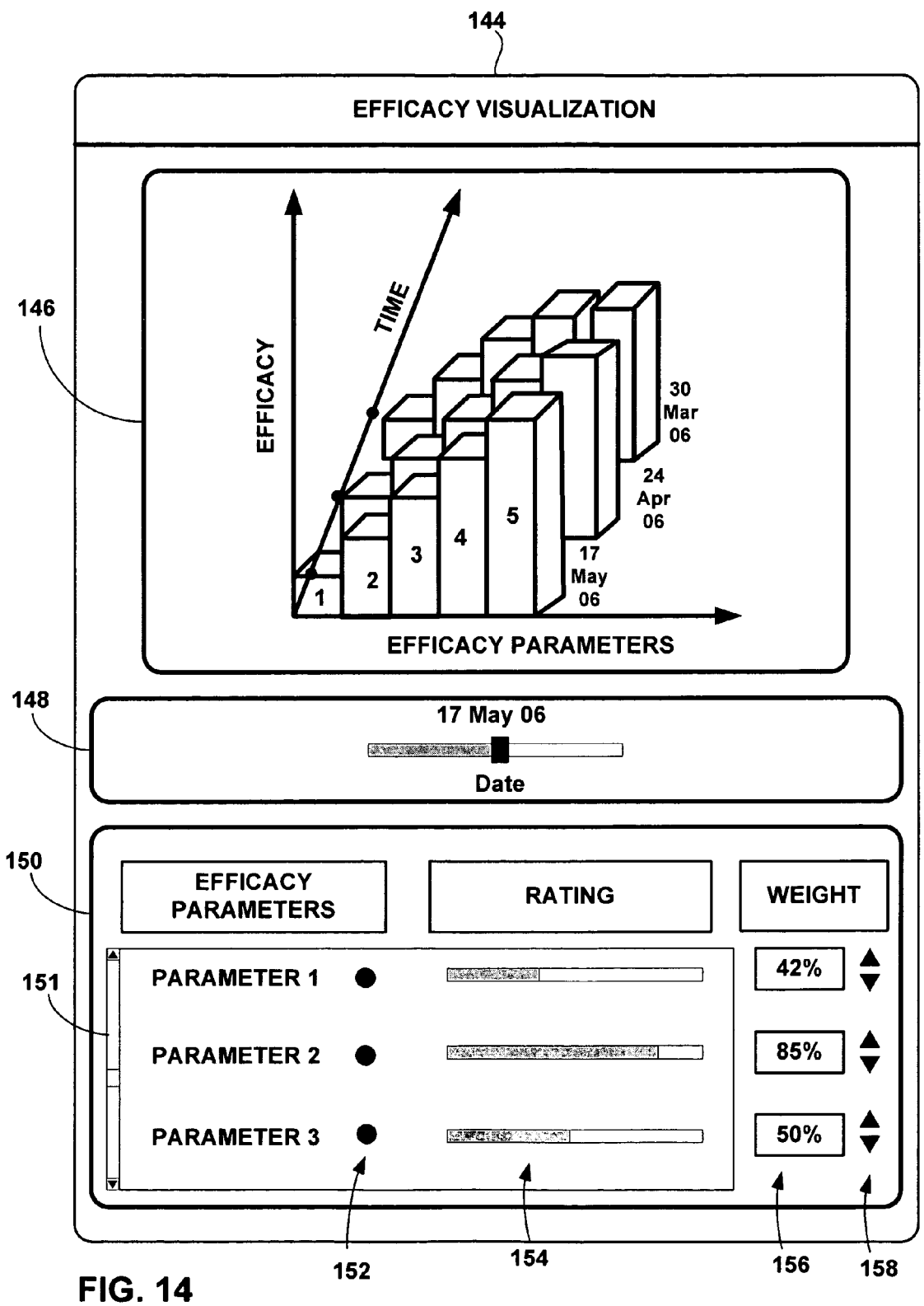
FIG. 14 is a diagram of a user interface for presenting a multi-axis bar graph visualization of efficacy ratings.

FIG. 14 is a diagram of a user interface for presenting a multi-axis bar graph visualization of efficacy ratings. User interface 144 may be presented by programmer 14 or programmer 16. As shown in FIG. 13, like the user interface 130 of FIG. 12, user interface 144 presents a graphic display area 146, a date adjustment interface 148, and efficacy parameter adjustment interface 150. The efficacy parameter adjustment interface 150 permits a user to select efficacy parameters for presentation in graphic display area 146, e.g., using checkboxes or radio buttons 152. In addition, efficacy parameter adjustment interface 150 may permit the user to adjust efficacy ratings for the parameters, e.g., using slider bars 154, and adjust the weightings applied to the efficacy parameter rating values, e.g., using text entry boxes 156 and/or up/down arrows 158. If not all parameters are visible within adjustment interface 150, a vertical scroll bar 151 may be provided to permit selective viewing of the list of parameters.

Graphic display area 146 presents a multi-axis bar graph representation of the efficacy parameters in which the value of each parameter, number 1-6 in area 146, is displayed as a vertical bar. Hence, the horizontal axis identifies each efficacy parameter, while the vertical axis indicates the value of each efficacy parameter. The diagonal axis shows a period of time.

In this manner, the graph shows values on the vertical axis for different sets of parameters on the horizontal axis over the period of time expressed on the diagonal axis. As in the case of FIG. 13, efficacy parameter values may be stored in memory and retrieved for multiple evaluation dates or times. The retrieved efficacy parameter values may be unweighted or weighted according to patient and/or clinician weighting values. In some embodiments, the user may be permitted to adjust the weightings for the current evaluation date as well as past evaluation dates.

In the example of FIG. 14, sets of efficacy parameter values are shown over a date range extending from the currently selected date, 17 May 2006, back to 24 Apr. 2006, and then to 30 Mar. 2006. In some embodiments, selection of a particular date may result in presentation of a set of parameter values for that date in front of other parameter value sets extending backward in time. Although display area 146 shows three different sets of parameter values, a lesser or greater number of parameter value sets may be displayed. In general, presentation of multiple parameter value sets in bar graph form provides another way to view progressive efficacy information or trends over a period of time. For example, FIG. 14 shows that the efficacy parameter value for parameter 5 has increased over the period between 30 Mar. 2006 and 17 May 2006. Hence, it may be inferred that the efficacy of the stimulation therapy has improved over that period of time.

Figure 15:
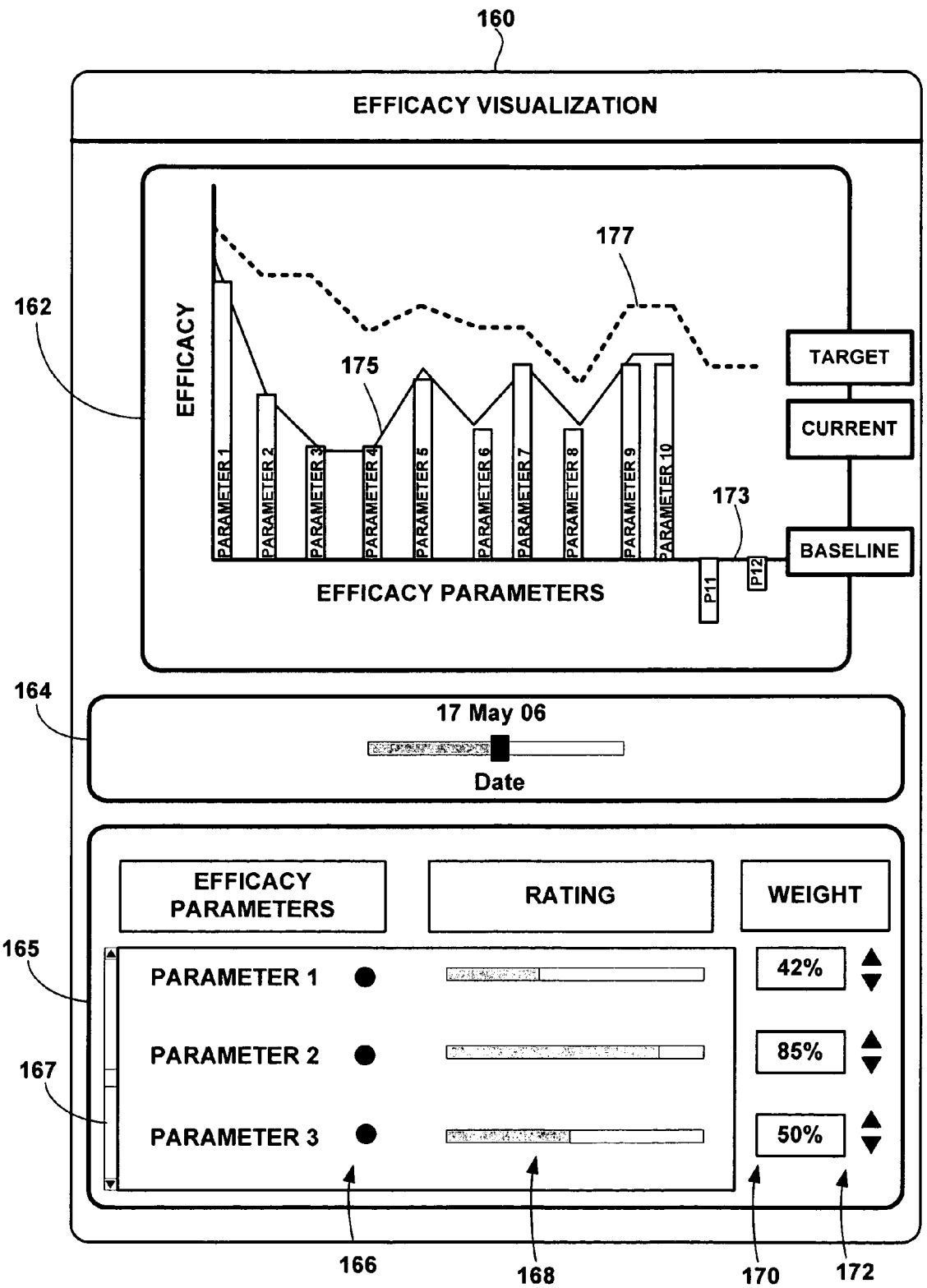
FIG. 15 is a diagram of a user interface for presenting a bar graph visualization of efficacy ratings.

FIG. 15 is a diagram of a user interface 160 for presenting a bar graph visualization of efficacy ratings. In the example of FIG. 15, user interface includes a graphical display area 162, a data adjustment area 164, and an efficacy parameter adjustment interface 165. The efficacy parameter adjustment interface 165 permits a user to select efficacy parameters for presentation in graphic display area 162, e.g., using checkboxes or radio buttons 166. In addition, efficacy parameter adjustment interface 165 may permit the user to adjust efficacy ratings for the parameters, e.g., using slider bars 168, and adjust the weightings applied to the efficacy parameter rating values, e.g., using text entry boxes 170 and/or up/down arrows 172. If not all parameters are visible within adjustment interface 165, a vertical scroll bar 167 may be provided to permit selective viewing of the list of parameters.

In the display area 162, user interface 160 presents a bar graph with two axes. The horizontal axis designates different parameters, e.g., parameters 1-12. The vertical axis designates the weighted efficacy value for each parameter. The zero value on the vertical axis may represent the baseline 173 for the patient. Curves for current and target efficacy rating values are designated by reference numerals 175 and 177, respectively, which may be normalized according to the baseline 173. The area under the curve 175 represents the current, overall efficacy rating for the patient. In the example of FIG. 15, bars 179 are provided only for the current efficacy rating values. Optionally, in some embodiments, efficacy parameter values may even be expressed as negative values, as indicated by parameters 11 and 12. If the efficacy parameter value drops below the baseline value 173, to a value that actually makes the efficacy value worse than the baseline, the result will be a negative bar.

Figure 16A:
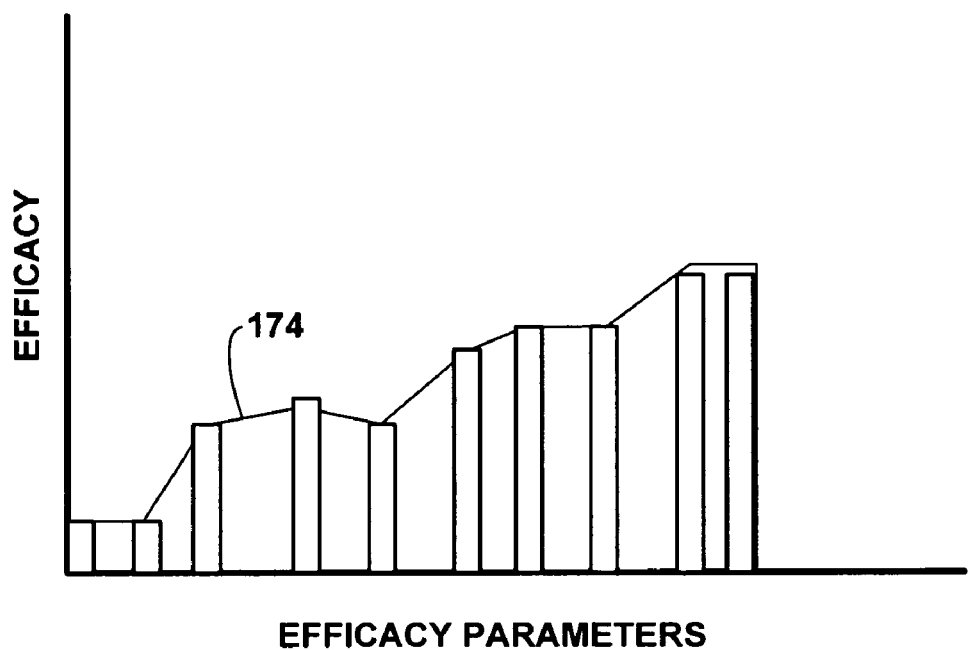
FIGS. 16A and 16B are graphs illustrating positive and negative bar graph visualizations of efficacy ratings.
Figure 16B:
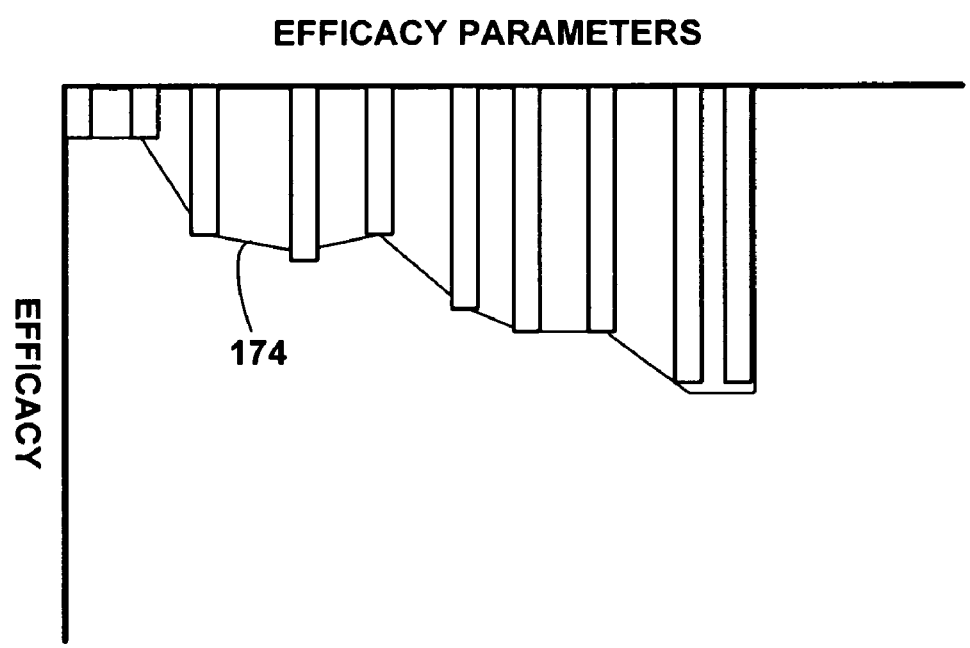

FIGS. 16A and 16B are graphs illustrating positive and negative bar graph visualizations of efficacy ratings. The graphs of FIGS. 16A and 16B may be displayed by a user interface, such as user interface 160 of FIG. 15. FIG. 16A represents presentation of different efficacy parameter values in a bar graph using a positive orientation in which efficacy value improvements are expressed as positive values relative to a baseline. FIG. 16B represents presentation of different efficacy parameter values in a bar graph using a negative orientation in which efficacy value improvements are expressed as negative values relative to a baseline. Each bar corresponds to a particular efficacy parameter. The bars define a curve 174.

In each case, different bars along the horizontal axis represents values for different, selected efficacy parameters. The area below the curve defined by the bars for the positive representation or above the curve for the negative representation provides a representation of the overall efficacy rating for the patient. A target set of bars and an associated curve also may be presented, if desired. Presentation of efficacy parameter values as negative values relative to a baseline may be more intuitive to some users, e.g., indicating that the severity of a baseline condition is being reduced. Accordingly, the display of stimulation parameter values with a positive or negative orientation may be an option for the user.

Figure 17:
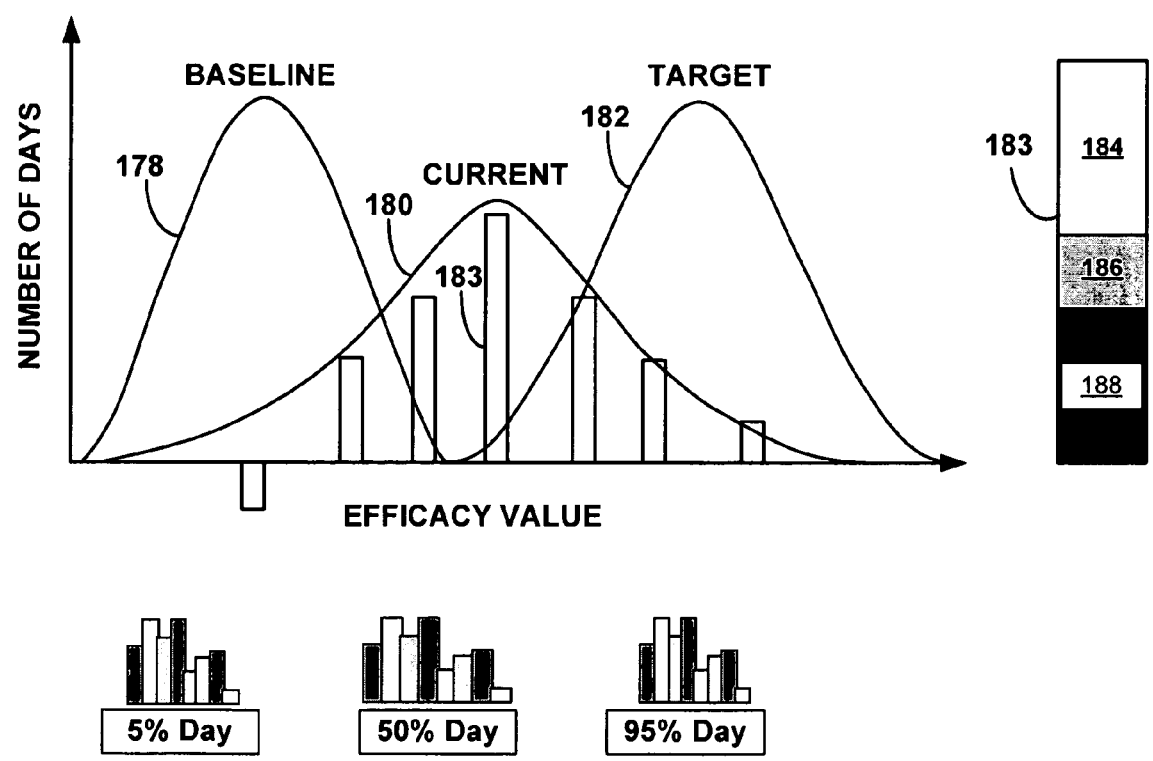
FIG. 17 is a graph illustrating histogram plot visualizations of efficacy ratings.

FIG. 17 is a graph illustrating histogram plot visualizations of efficacy ratings. The graph of FIG. 17 may be displayed by a user interface, such as user interface 160 of FIG. 15. FIG. 17 represents presentation of efficacy parameter value distributions for a baseline condition 178, current condition 180 and target condition 182. The horizontal axis represents efficacy value, and the vertical axis represents the number of days the efficacy value is at a particular value. Hence, each bar in the graph represents the number of days that the overall efficacy rating is at a particular efficacy value. The date range may be adjusted by the user so that distributions can viewed over different periods of time. As shown in FIG. 17, the baseline distribution 178 may be characterized by a distribution of values at the lower end of the efficacy value range, while the current distribution 180 may be in the midrange of the efficacy value range, and the target distribution may be toward a higher end of the efficacy value range.

In addition to the overall efficacy value distribution, additional distributions may be shown for 5% days, 50% days and 95% days in the pertinent date range. In particular, the 5%, 50%, and 95% charts show the per-parameter performance on an average 5th percentile day, 50th percentile day, and 95th percentile day. The mean and +/−2sigma or 3sigma would be similar assuming a normal distribution. This information can help the clinician understand how efficacy is in general and how efficacy is on the best and worst days.

Also, in some embodiments, each bar in the distribution may be divided into efficacy parameter value components. If incontinent episodes, urination frequency and nocturia are the pertinent efficacy parameters, for example, each bar in the distribution may also show the value for the individual parameters. For example, a given bar 183 may include efficacy parameter value components 184, 186, 188, where each component is sized to represent the size or proportion of the pertinent efficacy parameter value with the overall efficacy parameter value. For example, components 184, 186 and 188 may designate the relative proportions of the parameter values for incontinent episodes, urination frequency and nocturia within the overall efficacy parameter rating.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable logic arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions are executed to support one or more aspects of the functionality described in this disclosure.

Many embodiments of the invention have been described. Various modifications may be made without departing from the scope of the claims. For example, although the invention has been described with reference to electrical stimulation, and particularly stimulation for urinary incontinence as an illustration, the efficacy visualization and patient-individualized efficacy rating techniques may be used for other therapies, such as drug delivery therapy. Also, in some embodiments, the efficacy visualization and patient-individualized efficacy rating techniques may be used with external therapy devices, such as external stimulators or external drug delivery devices that are percutaneously coupled to leads or catheters, respectively.

Likewise, the invention may be applied to therapies for a variety of symptoms or conditions such as chronic pain, tremor, Parkinson's disease, epilepsy, urinary or fecal incontinence, sexual dysfunction, obesity, or gastroparesis, and may apply to electrical stimulation or drug delivery to a variety of tissue sites, such as the brain, the spinal cord, pelvic nerves, peripheral nerves, or the gastrointestinal tract of a patient.

Hence, stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES) to promote muscle movement or prevent atrophy.

These and other embodiments are within the scope of the following claims.

The invention claimed is:

1. A method comprising:
   receiving input, via at least one user interface of at least one device, that specifies a plurality of efficacy parameters from a set of selectable efficacy parameters associated with therapy delivered to a patient;
   receiving input, via the at least one user interface, that specifies a plurality of efficacy parameter values associated with the efficacy parameters, wherein at least one of the efficacy parameter values is specified for each of the efficacy parameters;
   receiving, via the at least one user interface, input specifying weighting values for the efficacy parameter values;
   generating, by at least one processor of the at least one device, weighted efficacy parameter values based on application of the weighting values to the efficacy parameter values; and
   displaying, via the at least one user interface, a multi-axis graphical representation of the weighted efficacy parameter values to provide a visualization of efficacy of the therapy, wherein each of the efficacy parameters is represented along a different axis of the multi-axis graphical representation, wherein each of the different axes of the multi-axis graphical representation references at least a common point.

2. The method of claim 1, further comprising displaying a boundary extending between the efficacy parameter values on multiple axes of the multi-axis graphical representation, wherein the boundary defines a shape.

3. The method of claim 2, wherein the multi-axis graphical representation includes three axes and the shape of the boundary is substantially triangular.

4. The method of claim 1, further comprising simultaneously displaying multiple multi-axis graphical representations of the weighted efficacy parameter values, wherein each of the multiple multi-axis graphical representations corresponds to the weighted efficacy parameter values obtained at different times.

5. The method of claim 1, further comprising:
   receiving input indicating a time reference for the weighted efficacy parameter values; and
   modifying the multi-axis graphical representation of the weighted efficacy parameter values to correspond to efficacy parameter values relating to the time reference.

6. The method of claim 1, wherein the therapy includes electrical stimulation therapy configured to relieve incontinence, and the efficacy parameters include one or more of incontinent episodes, urination frequency, and nocturia.

7. The method of claim 1, wherein the specified weighting values comprise at least a patient weighting value provided by a patient and a clinician weighting value provided by a clinician, and wherein the method further comprises:
   combining, by the at least one processor of the at least one device, the patient weighting value and the clinician weighting value to generate a weighted value that is based on both the patient weighting value and the clinician weighting value.

8. A device comprising:
   at least one processor that receives input specifying a plurality of efficacy parameters from a set of selectable efficacy parameters associated with therapy delivered to a patient, receives input specifying a plurality of efficacy parameter values associated with the efficacy parameters, wherein at least one of the efficacy parameter values is specified for each of the efficacy parameters, receives input specifying weighting values for the efficacy parameter values, and generates weighted efficacy parameter values based on application of the weighting values to the efficacy parameter values and;
   a user interface, generated by the at least one processor, that displays a multi-axis graphical representation of the weighted efficacy parameter values to provide a visualization of efficacy of the therapy, wherein each of the efficacy parameters is represented along a different axis of the multi-axis graphical representation, wherein each of the different axes of the multi-axis graphical representation references at least a common point.

9. The device of claim 8, wherein the user interface displays a boundary extending between the efficacy parameter values on multiple axes of the multi-axis graphical representation, wherein the boundary defines a shape.

10. The device of claim 9, wherein the multi-axis graphical representation includes three axes and the shape of the boundary is substantially triangular.

11. The device of claim 8, wherein the user interface simultaneously displays multiple multi-axis graphical representations of the weighted efficacy parameter values, and each of the multiple multi-axis graphical representations corresponds to the weighted efficacy parameter values obtained at different times.

12. The device of claim 8, wherein the user interface receives input indicating a time reference for the weighted efficacy parameter values, and wherein the at least one processor modifies the multi-axis graphical representation of the weighted efficacy parameter values to correspond to efficacy parameter values relating to the time reference.

13. The device of claim 8, wherein the therapy includes electrical stimulation therapy configured to relieve incontinence, and the efficacy parameters include one or more of incontinent episodes, urination frequency, and nocturia.

14. The device of claim 8, wherein the specified weighting values comprise at least a patient weighting value provided by a patient and a clinician weighting value provided by a clinician, and wherein the at least one processor combines the patient weighting value and the clinician weighting value to generate a weighted value that is based on both the patient weighting value and the clinician weighting value.

15. A non-transitory computer-readable storage medium comprising instructions to cause at least one processor to:
   receive input, via at least one user interface, that specifies a plurality of efficacy parameters from a set of selectable efficacy parameters associated with therapy delivered to a patient;
   receive input, via the at least one user interface, that specifies a plurality of efficacy parameter values associated with the efficacy parameters, wherein at least one of the efficacy parameter values is specified for each of the efficacy parameters;
   receive, via the at least one user interface, input specifying weighting values for the efficacy parameter values;
   generate weighted efficacy parameter values based on application of the weighting values to the efficacy parameter values; and
   display, via the at least one user interface, a multi-axis graphical representation of the weighted efficacy parameter values to provide visualization of efficacy of the therapy, wherein each of the efficacy parameters is represented along a different axis of the multi-axis graphical representation, wherein each of the different axes of the multi-axis graphical representation references at least a common point.

16. The non-transitory computer-readable storage medium of claim 15, further comprising instructions to cause the at least one processor to control the at least one user interface to display a boundary extending between the efficacy parameter values on multiple axes of the multi-axis graphical representation, wherein the boundary defines a shape, wherein the multi-axis graphical representation includes three axes and the shape of the boundary is substantially triangular.

17. The non-transitory computer-readable storage medium of claim 16, further comprising instructions to cause the at least one processor to control the at least one user interface to simultaneously display multiple multi-axis graphical representations of the weighted efficacy parameter values, wherein each of the multiple multi-axis graphical representations corresponds to the efficacy parameter values obtained at different times.

18. The non-transitory computer-readable storage medium of claim 15, wherein the therapy includes electrical stimulation therapy.

19. The non-transitory computer-readable storage medium of claim 15, wherein the specified weighting values comprise at least a patient weighting value provided by a patient and a clinician weighting value provided by a clinician, and wherein the computer-readable storage medium further comprising instructions to cause at least one processor to:
   combine the patient weighting value and the clinician weighting value to generate a weighted value that is based on both the patient weighting value and the clinician weighting value.

20. A method comprising:
   receiving input, via at least one user interface of at least one device, that specifies a plurality of efficacy parameters associated with therapy delivered to a patient;
   receiving input, via the at least one user interface, that specifies a plurality of efficacy parameter values associated with the efficacy parameters, wherein at least one of the efficacy parameter values is specified for each of the efficacy parameters;
   receiving, via the at least one user interface, input specifying weighting values for the efficacy parameter values;
   generating, by at least one processor of the at least one device, weighted efficacy parameter values based on application of the weighting values to the efficacy parameter values;
   displaying, via the at least one user interface, a multi-axis graphical representation of the weighted efficacy parameter values to provide a visualization of efficacy of the therapy, wherein each of the efficacy parameters is represented along a different axis of the multi-axis graphical representation, wherein each of the different axes of the multi-axis graphical representation references at least a common point;
   receiving input specifying a time reference for the weighted efficacy parameter values; and
   modifying, by at least one processor of the at least one device, the multi-axis graphical representation of the weighted efficacy parameter values to correspond to efficacy parameter values relating to the time reference.

21. The method of claim 20, wherein the multi-axis graphical representation includes a bar graph.

22. The method of claim 20, further comprising simultaneously displaying multiple multi-axis graphical representations for efficacy parameter values relating to different time references.

23. The method of claim 20, wherein the therapy includes electrical stimulation therapy.

24. The method of claim 20, wherein the specified weighting values comprise at least a patient weighting value provided by a patient and a clinician weighting value provided by a clinician, and wherein the method further comprises:
   combining, by the at least one processor of the at least one device, the patient weighting value and the clinician weighting value to generate a weighted value that is based on both the patient weighting value and the clinician weighting value.

25. A device comprising:
   at least one processor; and
   a user interface that:
      receives input specifying the efficacy parameters that are associated with therapy delivered to a patient;
      receives input that specifies the efficacy parameter values associated with the efficacy parameters, wherein at least one of the efficacy parameter values is specified for each of the efficacy parameters;
      receives input specifying weighting values for the efficacy parameter values;
      displays a multi-axis graphical representation of weighted efficacy parameter values to provide a visualization of efficacy of the therapy, wherein each of the efficacy parameters is represented along a different axis of the multi-axis graphical representation, wherein each of the different axes of the multi-axis graphical representation references at least a common point; and
      receives input specifying a time reference for the weighted efficacy parameter values, wherein the at least one processor generates the weighted efficacy parameter values based on application of the weighting values to the efficacy parameter values, and wherein the at least one processor modifies the multi-axis graphical representation of the weighted efficacy parameter values to correspond to efficacy parameter values relating to the time reference.

26. The device of claim 25, wherein the multi-axis graphical representation includes a bar graph.

27. The device of claim 25, wherein the user interface simultaneously displays multiple multi-axis graphical representations for efficacy parameter values relating to different time references.

28. The device of claim 25, wherein the therapy includes electrical stimulation therapy.

29. The device of claim 25, wherein the specified weighting values comprise at least a patient weighting value provided by a patient and a clinician weighting value provided by a clinician, and wherein the processor combines the patient weighting value and the clinician weighting value to generate a weighted value that is based on both the patient weighting value and the clinician weighting value.

30. A device comprising:
   means for receiving input specifying of a plurality of efficacy parameters from a set of selectable efficacy parameters associated with therapy delivered to a patient;
   means for receiving input specifying a plurality of efficacy parameter values associated with the efficacy parameters, wherein at least one of the efficacy parameter values is specified for each of the efficacy parameters;
   means for receiving input specifying weighting values for the efficacy parameter values;
   means for generating weighted efficacy parameter values based on application of the weighting values to the efficacy parameter values; and
   means for displaying a multi-axis graphical representation of the weighted efficacy parameter values to provide visualization of efficacy of the therapy, wherein each of the efficacy parameters is represented along a different axis of the multi-axis graphical representation, wherein each of the different axes of the multi-axis graphical representation references at least a common point.

31. A non-transitory computer-readable storage medium comprising instructions to cause at least one processor to:
   receive input specifying the efficacy parameters that are associated with therapy delivered to a patient;
   receive input that specifies the efficacy parameter values associated with the efficacy parameters, wherein at least one of the efficacy parameter values is specified for each of the efficacy parameters;
   receive input specifying weighting values for the efficacy parameter values;
   display a multi-axis graphical representation of weighted efficacy parameter values to provide a visualization of efficacy of the therapy, wherein each of the efficacy parameters is represented along a different axis of the multi-axis graphical representation, wherein each of the different axes of the multi-axis graphical representation references at least a common point; and
   receive input specifying a time reference for the weighted efficacy parameter values,
   wherein the processor generates the weighted efficacy parameter values based on application of the weighting values to the efficacy parameter values, and
   wherein the processor modifies the multi-axis graphical representation of the weighted efficacy parameter values to correspond to efficacy parameter values relating to the time reference.

32. The non-transitory computer-readable storage medium of claim 31, wherein the specified weighting values comprise at least a patient weighting value provided by a patient and a clinician weighting value provided by a clinician, the computer-readable storage medium further comprising instructions to cause the at least one processor to:
   combine the patient weighting value and the clinician weighting value to generate a weighted value that is based on both the patient weighting value and the clinician weighting value.

\* \* \* \* \*